(12) United States Patent
Wang et al.

(10) Patent No.: US 8,268,818 B2
(45) Date of Patent: Sep. 18, 2012

(54) INHIBITORS OF C-MET AND USES THEREOF

(75) Inventors: Tiansheng Wang, Concord, MA (US); Jeremy Green, Waltham, MA (US); Brian Ledford, Attleboro, MA (US); François Maltais, Tewksbury, MA (US); Andreas P. Termin, San Diego, CA (US); Mark Cornebise, Watertown, MA (US); Jonathan Parsons, Arlington, MA (US); Adam Tanner, Abingdon (GB); James Westcott, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 177 days.

(21) Appl. No.: 12/438,995

(22) PCT Filed: Sep. 4, 2007

(86) PCT No.: PCT/US2007/019261
§ 371 (c)(1),
(2), (4) Date: Feb. 5, 2010

(87) PCT Pub. No.: WO2008/027584
PCT Pub. Date: Mar. 6, 2008

(65) Prior Publication Data
US 2010/0144721 A1    Jun. 10, 2010

Related U.S. Application Data

(60) Provisional application No. 60/841,935, filed on Sep. 1, 2006.

(51) Int. Cl.
*A61K 31/427* (2006.01)
*A61K 31/454* (2006.01)
*A61K 31/495* (2006.01)
*A61K 31/497* (2006.01)
*C07D 413/14* (2006.01)
*C07D 405/14* (2006.01)
*C07D 277/44* (2006.01)

(52) U.S. Cl. ............. 514/227.8; 514/236.8; 514/254.02; 514/326; 514/371; 544/369; 544/69; 544/133; 546/209; 548/195

(58) Field of Classification Search ............... 514/227.8, 514/236.8, 254.02, 326, 371; 544/369, 60, 544/133; 546/209; 548/195
See application file for complete search history.

(56) References Cited

U.S. PATENT DOCUMENTS
5,308,857 A * 5/1994 Takasugi et al. ............. 514/370

FOREIGN PATENT DOCUMENTS
| EP | 1700856 | 9/2006 |
| WO | 03072557 | 9/2003 |
| WO | 2004078754 | 9/2004 |
| WO | 2004096797 | 11/2004 |
| WO | 2006051270 | 5/2006 |

OTHER PUBLICATIONS

Echeverria et al., Med. Res. Rev 2000, 20(1), 28-57.*
Usova, E.B., et al.; "Synthesis of 5-(5-substituted 2-furyl)thiazole derivatives by reaction of 2-(5-substituted furfuryl) thiuronium salts and acetic anhydride" Khimiya Geterotsiklicheskikh Soedinenii, vol. 4, 1990, pp. 557-562, XP009095544.
PCT/US2007/019261: International Search Report, Apr. 14, 2008.

* cited by examiner

*Primary Examiner* — Jason M Nolan
(74) *Attorney, Agent, or Firm* — Daniel A. Pearson

(57) ABSTRACT

The present invention relates to compounds useful as inhibitors of PI3K, particularly of PI3Kγ. The invention also provides pharmaceutically acceptable compositions comprising said compounds and methods of using the compositions in the treatment of various disease, conditions, or disorders.

18 Claims, No Drawings

INHIBITORS OF C-MET AND USES THEREOF

CROSS-REFERENCE TO RELATED APPLICATIONS

This present application claims the benefit, under 35 U.S.C. §119, to U.S. Provisional Application No. 60/841,935, filed Sep. 1, 2006, and under 35 U.S.C. §371 to International Patent Application No. PCT/US2007/019261, filed Sep. 4, 2007, the entire disclosures of which are incorporated herein by reference.

TECHNICAL FIELD OF THE INVENTION

The present invention relates to compounds useful as inhibitors of phosphatidylinositol 3-kinase (PI3K). The invention also provides pharmaceutically acceptable compositions comprising the compounds of the invention and methods of using the compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)$P_2$, PIP2] and PI 3,4,5-trisphosphate [PI(3,4,5)$P_3$, PIP3]. PI(3,4)$P_2$ and PI(3,4,5)$P_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with αγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K inhibitors have been developed, there is a need for additional compounds to inhibit PI3Ks for treating various disorders and diseases. Accordingly, it would be desirable to develop additional compounds that are useful as inhibitors of PI3K.

SUMMARY OF THE INVENTION

It has now been found that compounds of this invention, and pharmaceutically acceptable compositions thereof, are effective as inhibitors of PI3K, particularly PI3Kγ. These compounds have the general formula I:

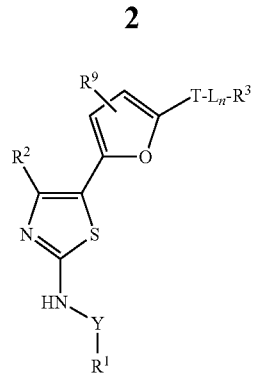

or a pharmaceutically acceptable salt thereof, wherein $R^1$, $R^2$, $R^3$, $R^9$, Y, T, L and n are as defined herein.

These compounds, and pharmaceutically acceptable compositions thereof, are useful for treating or lessening the severity of a variety of disorders, including cancer, autoimmune diseases, inflammatory diseases, cardiovascular diseases, diabetes, allergic diseases, asthma or organ transplantation rejection in a patient.

The compounds and compositions provided by this invention are also useful for the study of PI3K in biological and pathological phenomena; the study of intracellular signal transduction pathways mediated by such kinases; and the comparative evaluation of new kinase inhibitors.

The invention also provides assays for identifying inhibitors of PI3K.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and In yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "carbocyclyl") refers to a hydrocarbon that is completely saturated or that contains one or more units of unsaturation, but which is not aromatic, that has a single point of attachment to the rest of the molecule, and wherein any individual ring in said bicyclic ring system has 3-7 members. Unless otherwise specified, the term "cycloaliphatic" refers to a monocyclic $C_3$-$C_8$ hydrocarbon or bicyclic $C_8$-$C_{12}$ hydrocarbon. Suitable cycloaliphatic groups include, but are not limited to, cycloalkyl, cycloalkenyl, and cycloalkynyl. Further examples of aliphatic groups include cyclopropyl, cyclobutyl, cyclopentyl, cyclopentenyl, cyclohexyl, cyclohexenyl, cycloheptyl, and cycloheptenyl.

The term "heterocycle", "heterocyclyl" or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl" or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definitions of $R^2$ and $R^4$ below. Other suitable substituents include: halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$;

—NR°NR°C(O)R°;     —NR°NR°C(O)N(R°)$_2$; —NR°NR°CO$_2$R°;  —C(O)C(O)R°;  —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°) R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$ aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R* is unsubstituted.

In some embodiments, optional substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), 0(halo C$_{1-4}$ aliphatic), or halo(C$_{1-4}$ aliphatic), wherein each of the foregoing C$_{1-4}$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

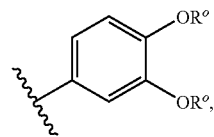

these two occurrences of R° are taken together with the oxygen atoms to which they are bound to form a fused 6-membered oxygen containing ring:

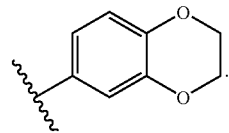

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

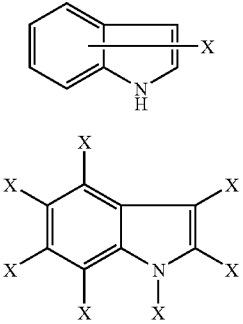

Figure a

Figure b

This also applies to multiple ring systems fused to optional ring systems (which would be represented by dotted lines). For example, in Figure c, X is an optional substituent both for ring A and ring B.

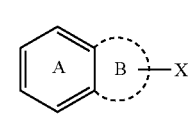

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

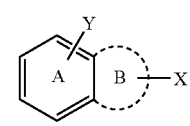

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Description of Compounds of the Invention

The present invention relates to a compound of formula I:

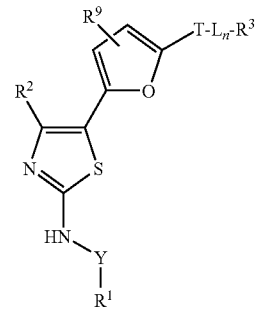

I or a pharmaceutically acceptable salt thereof, wherein:

Y is —C(O)— or a bond;

$R^1$ is a $C_{1-6}$ aliphatic, a $C_{3-10}$ monocyclic or bicyclic cycloaliphatic, a $C_{6-10}$ monocyclic or bicyclic aryl, a 5-10 membered monocyclic or bicyclic heteroaryl, or a 5-10 membered monocyclic or bicyclic heterocyclyl, wherein $R^1$ is optionally substituted with 1-6 occurrences of $J^{R1}$;

each $J^{R1}$ is independently selected from halogen, OH, OR, $NO_2$, $NH_2$, NHR, $NR_2$, SH, SR, CN, $C(O)NH_2$, C(O)NHR, $C(O)NR_2$, C(O)OH, C(O)OR, NHC(O)H, NHC(O)R, NRC(O)H, NRC(O)R, NHC(O)OH, NHC(O)OR, NRC(O)OH, NRC(O)OR, or R; or two $J^{R1}$, together with the carbon(s) to which they are attached, form a cyclopropyl ring or C=O;

each R is independently selected from a $C_{1-4}$ aliphatic or $C_{3-4}$ cycloaliphatic optionally substituted with 1-4 occurrences of halogen, OH, $NO_2$, $NH_2$, SH or CN;

$R^2$ is H or a $C_{1-6}$ aliphatic or $C_{3-6}$ cycloaliphatic, wherein $R^2$ is optionally substituted with 1-4 occurrences of $J^{R2}$;

each $J^{R2}$ is independently selected from halogen, OH, OR, $NO_2$, $NH_2$, NHR, $NR_2$, SH, SR, CN, $C(O)NH_2$, C(O)NHR, $C(O)NR_2$, C(O)OH, C(O)OR, NHC(O)H, NHC(O)R, NRC(O)H, NRC(O)R, NHC(O)OH, NHC(O)OR, NRC(O)OH, NRC(O)OR, or R; or two $J^{R2}$, together with the carbon(s) to which they are attached, form a cyclopropyl ring or C=O;

T is —$SO_2NR^4$—, —$CONR^4$— or —C(O)O—;

$R^4$ is H or a $C_{1-6}$ aliphatic or $C_{3-7}$ cycloaliphatic optionally substituted with 1-6 occurrences of $J^{R4}$;

each $J^{R4}$ is independently selected from halogen, OH, OR', $NO_2$, $NH_2$, NHR', $NR'_2$, SH, SR', CN, 5-6 membered aryl or heteroaryl, or R'; or two $J^{R4}$, together with the carbon(s) to which they are attached, form a cyclopropyl ring or C=O;

each R' is independently selected from a $C_{1-6}$ aliphatic or $C_{3-7}$ cycloaliphatic optionally substituted with 1-6 occurrences of halogen, OH, $NO_2$, $NH_2$, SH or CN;

L is a $C_{1-6}$ aliphatic wherein up to three methylene units are replaced by —NH—, —$NR^5$—, —O—, —S—, —$CO_2$—, —OC(O)—, —C(O)CO—, —C(O)—, —C(O)NH—, —C(O)$NR^5$—, —NC(=N—CN)N, —NHCO—, —$NR^5$CO—, —NHC(O)O—, —$NR^5$C(O)O—, —$SO_2$NH—, —$SO_2NR^5$—, —$NHSO_2$—, —$NR^5SO_2$—, —NHC(O)NH—, —$NR^5$C(O)NH—, —NHC(O)$NR^5$—, —$NR^5$C(O)$NR^5$, —OC(O)NH—, —OC(O)$NR^5$—, —$NHSO_2$NH—, —$NR^5SO_2$NH—, —$NHSO_2NR^5$—, —$NR^5SO_2NR^5$—, —SO—, or —$SO_2$—, wherein L is optionally substituted with 1-4 occurrences of $R^6$;

each $R^5$ is independently selected from $C_{1-6}$ aliphatic, $C_{3-10}$ monocyclic or bicyclic cycloaliphatic, $C_{6-10}$ monocyclic or bicyclic aryl, 5-10 membered monocyclic or bicyclic heteroaryl, or 5-10 membered monocyclic or bicyclic heterocyclyl; or two R⁵ groups, on the same substituent or different substituents, together with the atom(s) to which each R⁵ group is bound, form a 3-8 membered heterocyclyl;

each R⁶ is independently selected from halogen, OH, OR', NO₂, NH₂, NHR', NR'₂, SH, SR', CN, or R'; or two R⁶, together with the carbon(s) to which they are attached, form a cyclopropyl ring or C=O;

n is 0 or 1;

R³ is H or an optionally substituted group selected from a C$_{1-6}$ aliphatic, a C$_{3-10}$ monocyclic or bicyclic cycloaliphatic, a C$_{6-10}$ monocyclic or bicyclic aryl, a 5-10 membered monocyclic or bicyclic heteroaryl, or a 5-10 membered monocyclic or bicyclic heterocyclyl, wherein R³ is optionally substituted with 1-6 occurrences of J$^{R3}$, or R³ and R⁴, together with the nitrogen to which R⁴ is attached, form a 5-10 membered monocyclic or bicyclic heterocyclyl or heteroaryl; wherein n is 0 and said heterocyclyl or heteroaryl is optionally substituted with 1-6 occurrences of J$^{R3}$;

each J$^{R3}$ is independently selected from —(U)$_m$—X;

U is a C$_{1-4}$ aliphatic, wherein up to two methylene units are optionally and independently replaced by G$^U$ and wherein U is optionally substituted with 1-4 J$^U$;

G$^U$ is —NH—, —NR⁷—, —O—, —S—, —CO₂—, —OC(O)—, —C(O)CO—, —C(O)—, —C(O)NH—, —C(O)NR⁷—, —NC(=N—CN)N—, —NHCO—, —NR⁷CO—, —NHC(O)O—, —NR⁷C(O)O—, —SO₂NH—, —SO₂NR⁷—, —NHSO₂—, —NR⁷SO₂—, —NHC(O)NH—, —NR⁷C(O)NH—, —NHC(O)NR⁷—, —NR⁷C(O)NR⁷, —OC(O)NH—, —OC(O)NR⁷—, —NHSO₂NH—, —NR⁷SO₂NH—, —NHSO₂NR⁷—, —NR⁷SO₂NR⁷—, —SO—, or —SO₂—;

R⁷ is C$_{1-6}$ aliphatic or C$_{3-7}$ cycloaliphatic optionally substituted with 1-6 occurrences of halogen, OH, NO₂, NH₂, SH or CN;

m is 0 or 1;

each J$^U$ is independently selected from halogen, OH, OR', NO₂, NH₂, NHR', NR'₂, SH, SR', CN, or R'; or two J$^U$, together with the carbon(s) to which they are attached, form a cyclopropyl ring or C=O;

X is H, halogen, OH, OR, NO₂, NH₂, NHR, NR₂, SH, SR, CN, C(O)NH₂, C(O)NHR, C(O)NR₂, C(O)OH, C(O)OR, NHC(O)H, NHC(O)R, NRC(O)H, NRC(O)R, NHC(O)OH, NHC(O)OR, NRC(O)OH, NRC(O)OR, or a group selected from a C$_{1-6}$ aliphatic, a C$_{3-10}$ monocyclic or bicyclic cycloaliphatic, a C$_{6-10}$ monocyclic or bicyclic aryl, a 5-10 membered monocyclic or bicyclic heteroaryl, or a 5-10 membered monocyclic or bicyclic heterocyclyl, wherein said group is optionally substituted with 1-4 J$^X$, or two X, together with the carbon(s) to which they are attached, form a cyclopropyl ring or CO=O; wherein X is not H when m is 0;

each J$^X$ is independently selected from halogen, OH, OR, NO₂, NH₂, NHR, NR₂, SH, SR, CN, C(O)NH₂, C(O)NHR, C(O)NR₂, C(O)OH, C(O)OR, NHC(O)H, NHC(O)R, NRC(O)H, NRC(O)R, NHC(O)OH, NHC(O)OR, NRC(O)OH, NRC(O)OR; and R⁹ is selected from H; halogen; OH; NO₂; NH₂; SH; CN; or a group selected from a C$_{1-6}$ aliphatic or a C$_{3-7}$ cycloaliphatic, wherein said group is optionally substituted with 1-6 occurrences of halogen, OH, NO₂, NH₂, SH or CN.

In one embodiment, Y is C(O) and the compound is of formula II:

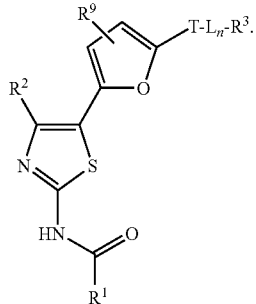

II

In one embodiment of either of the above formulae, R¹ is a C$_{1-6}$ aliphatic optionally substituted with 1-6 occurrences of J$^{R1}$. In a further embodiment, R¹ is a C$_{1-3}$ aliphatic optionally substituted with 1-3 occurrences of J$^{R1}$. In yet a further embodiment, R¹ is a C$_{1-3}$ aliphatic. In still a further embodiment, R¹ is CH₃, CH₂CH₃ or cyclopropyl.

In one embodiment of either of the above formulae or compounds, R² is C$_{1-3}$ aliphatic, wherein R² is optionally substituted with 1-3 occurrences of J$^{R2}$. In a further embodiment, R² is C$_{1-3}$ aliphatic. In yet a further embodiment, R² is CH₃.

In one embodiment of any of the above formulae or compounds, said compound is of formula IIIa, IIIb or IIIc:

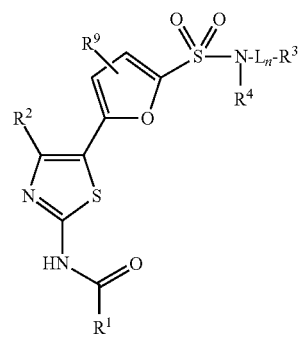

IIIa

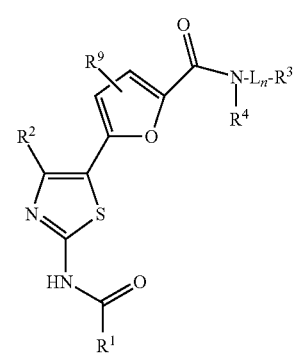

IIIb

In one embodiment of any of the above formulae or compounds, said compound is of formula IIIa', IIIb' or IIIc':

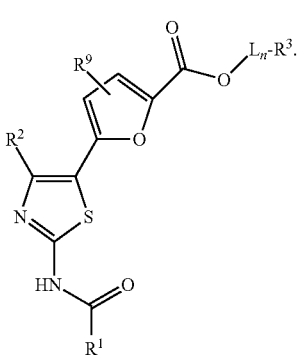

IIIa'

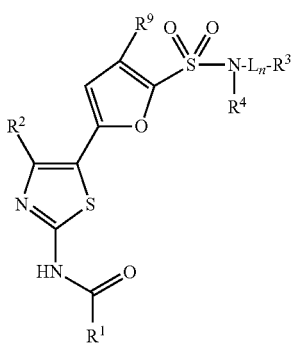

IIIb'

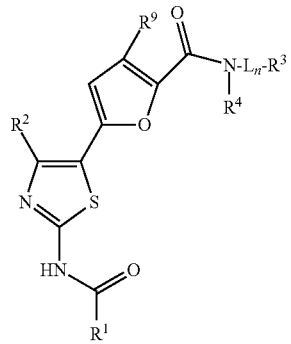

IIIc'

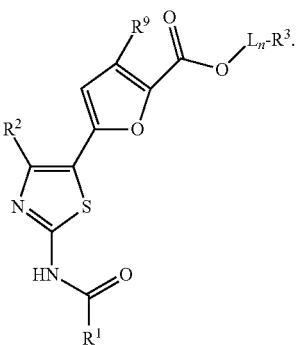

In one embodiment of the above formulae or compounds, $R^3$ and $R^4$, together with the nitrogen to which $R^4$ is attached, form a 5-10 membered monocyclic or bicyclic heterocyclyl or heteroaryl; wherein said heterocyclyl or heteroaryl is optionally substituted with 1-6 occurrences of $J^{R3}$. In a further embodiment, said heterocyclyl or heteroaryl formed by $R^3$ and $R^4$ is a 5-6 membered monocyclic heterocyclyl or 9-10 membered heterocyclyl or heteroaryl; wherein said monocyclic or bicyclic heterocyclyl or bicyclic heteroaryl contains 1-3 heteroatoms and is optionally substituted with 1-3 occurrences of $J^{R3}$. In yet a further embodiment, said monocyclic or bicyclic heterocyclyl or bicyclic heteroaryl contains 1-2 heteroatoms and is optionally substituted with 1-2 occurrences of $J^{R3}$. In a still further embodiment, said monocyclic or bicyclic heterocyclyl or bicyclic heteroaryl is selected from the following:

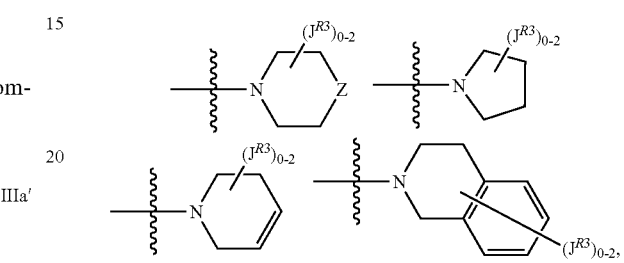

wherein Z is $CH_2$, NH, O or S, and wherein the hydrogens of said $CH_2$ of Z is optionally substituted by 1-2 occurrences of $J^{R3}$ and the hydrogen of said NH of Z is optionally substituted by $J^{R3}$.

In a further embodiment, each occurrence of $J^{R3}$ is selected from $J^{R3}$ is selected from halogen; OH; OR; CN; $NH_2$; NHR; $NR_2$; $C(O)NH_2$; C(O)NHR; $C(O)NR_2$; NHCOR; C(O)OR; C(O)OH; oxo; $(CH_2)_{0-3}$-phenyl optionally substituted with halogen, OH, OR, $NO_2$, $NH_2$, SH or CN; or $C_{1-4}$ aliphatic optionally substituted with halogen, OH, OR, $NO_2$, $NH_2$, SH or CN.

In another embodiment of the above formulae or compounds, $R^3$ is H or an optionally substituted group selected from a $C_{1-6}$ aliphatic, a $C_{3-10}$ monocyclic or bicyclic cycloaliphatic, a $C_{6-10}$ monocyclic or bicyclic aryl, a 5-10 membered monocyclic or bicyclic heteroaryl, or a 5-10 membered monocyclic or bicyclic heterocyclyl, wherein $R^3$ is optionally substituted with 1-6 occurrences of $J^{R3}$. In a further embodiment, n is 1 and L is a $C_{1-3}$ aliphatic optionally substituted with 1-2 occurrences of R'. In yet a further embodiment, L is —$CH_2$— or CH substituted with a $C_{1-2}$ aliphatic, which $C_{1-2}$ aliphatic is optionally substituted with 1-2 occurrences of halogen, OH, $NO_2$, $NH_2$, SH or CN. In a still further embodiment, L is —$CH_2$—. In another embodiment, n is 0.

In embodiment, $R^3$ is a $C_{1-4}$ aliphatic, a $C_{3-6}$ monocyclic cycloaliphatic, phenyl, a 5-6 membered monocyclic heteroaryl, or a 5-10 membered monocyclic or bicyclic heterocyclyl, wherein $R^3$ is optionally substituted with 1-4 occurrences of $J^{R3}$. In a further embodiment, $R^3$ is a $C_{1-4}$ aliphatic, a $C_{3-6}$ monocyclic cycloaliphatic, phenyl, a 5-6 membered monocyclic heteroaryl, or a 5-6 membered monocyclic heterocyclyl, wherein $R^3$ is optionally substituted with 1-4 occurrences of $J^{R3}$.

In a further embodiment, each occurrence of $J^{R3}$ is selected from halogen; OH; OR; CN; $NH_2$; NHR; $NR_2$; $C(O)NH_2$; C(O)NHR; $C(O)NR_2$; NHCOR; C(O)OR; C(O)OH; oxo; $(CH_2)_{0-3}$phenyl optionally substituted with halogen, OH, OR, $NO_2$, $NH_2$, SH or CN; or $C_{1-4}$ aliphatic optionally substituted with halogen, OH, OR, $NO_2$, $NH_2$, SH or CN.

In one embodiment of any of the above formulae or compounds, $R^4$ is H or $C_{1-3}$ aliphatic optionally substituted with one occurrence of $J^{R4}$. In a further embodiment, $R^4$ is H, $CH_3$, $CH_2CH_3$, $CH_2CH_2OH$, $CH_2CHCH_2$, cyclopropyl or $CH_2$phenyl. In yet a further embodiment, $R^4$ is H or $CH_3$.

In one embodiment of any of the above formulae or compounds, $R^8$ is selected from H, cyclopropyl, or a $C_{1-3}$ aliphatic optionally substituted with 1-3 occurrences of halogen or OH. In a further embodiment, $R^8$ is selected from H, halogen, methyl or ethyl. In yet a further embodiment, $R^8$ is H.

In one embodiment of any of the above formulae or compounds, $R^9$ is selected from H, OH, halogen, cyclopropyl, or a $C_{1-3}$ aliphatic optionally substituted with 1-3 occurrences of halogen or OH. In a further embodiment, $R^9$ is selected from H, OH, halogen, methyl or ethyl. In yet a further embodiment, $R^9$ is H or methyl.

In another embodiment, the invention provides a compound of Table 1 or Table 2:

TABLE 1

1

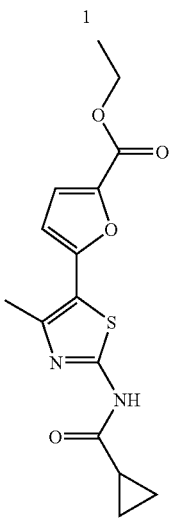

2

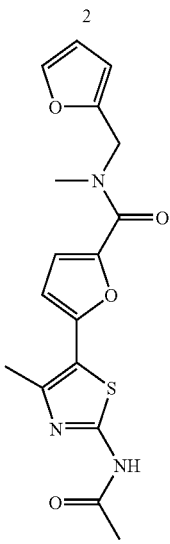

TABLE 1-continued

3

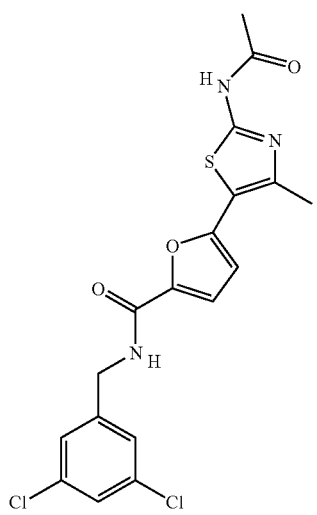

4

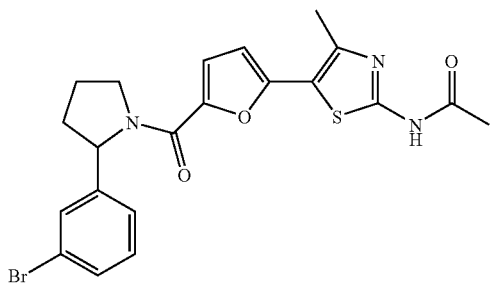

5

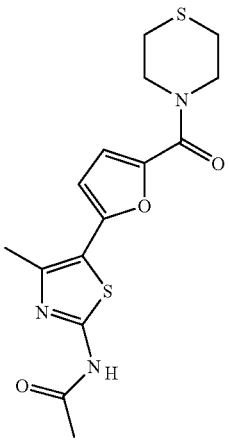

TABLE 1-continued
6
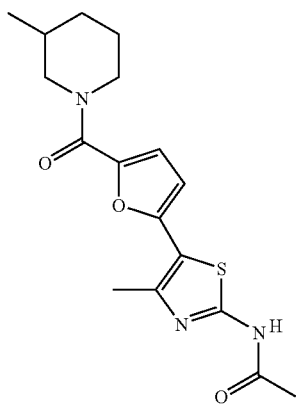
7
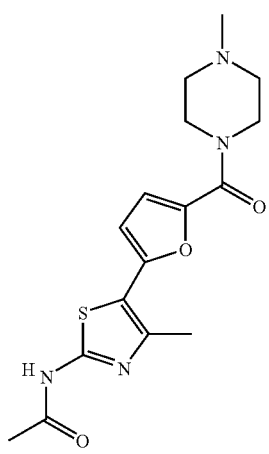
8
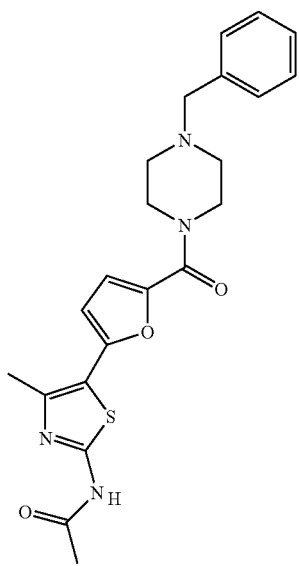
TABLE 1-continued
9
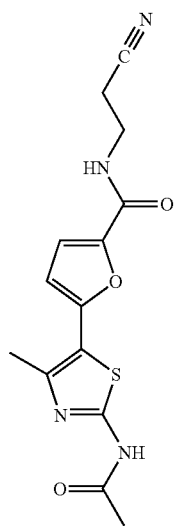
10
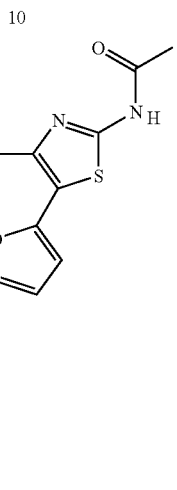
11
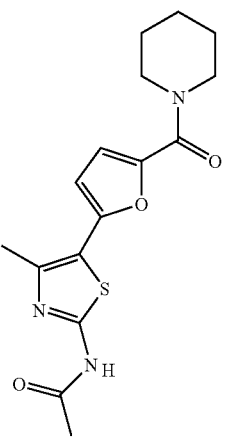

TABLE 1-continued
12
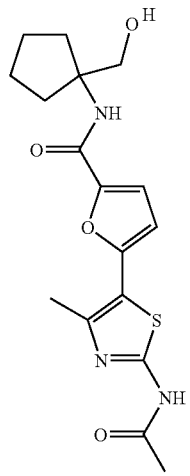
13
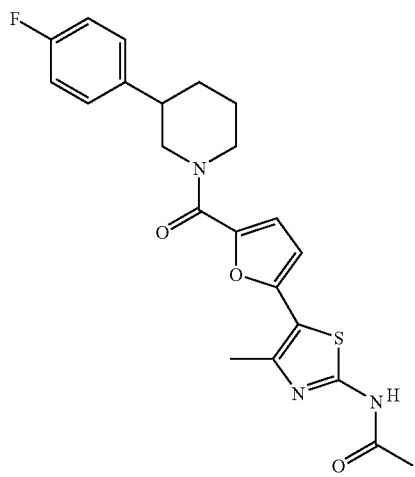
14
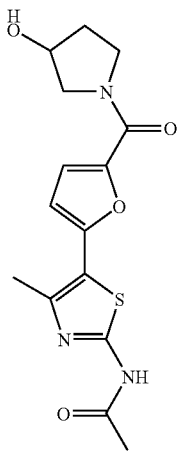
TABLE 1-continued
15
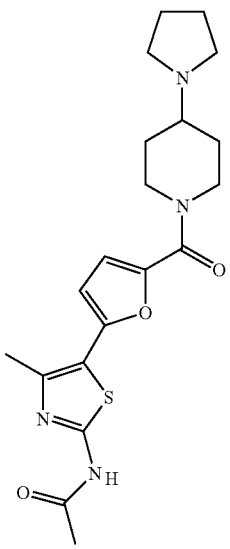
16
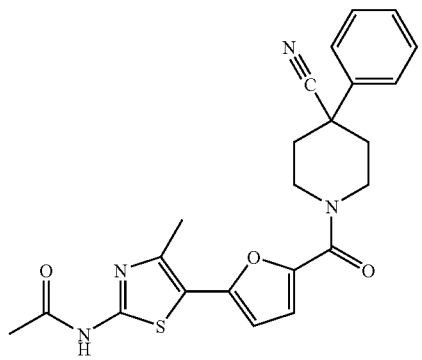
17
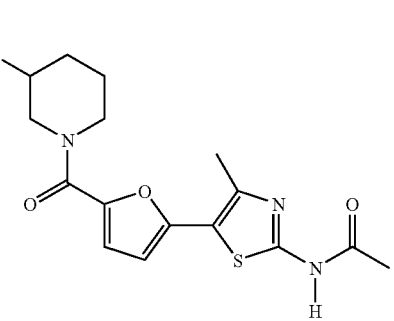

TABLE 1-continued
18
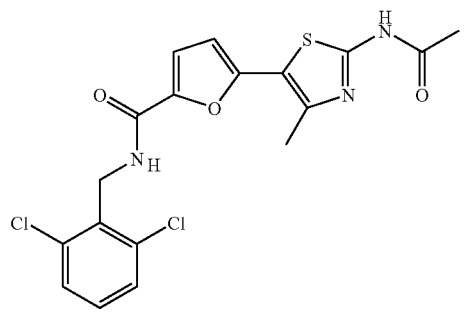
19
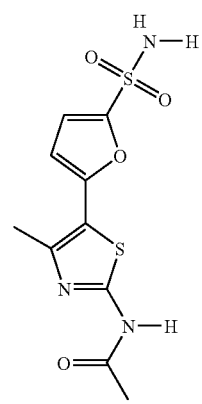
20
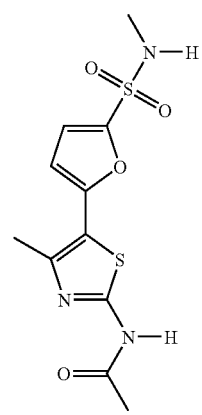
21
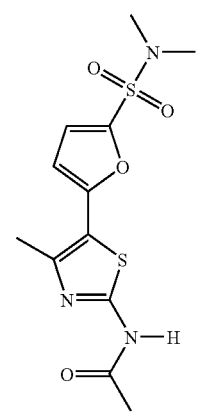
TABLE 1-continued
22
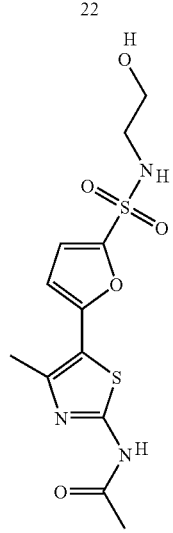
23
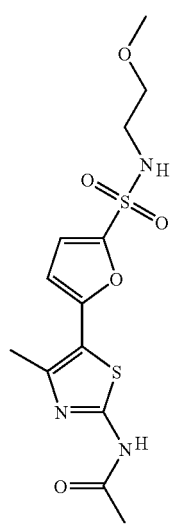
24
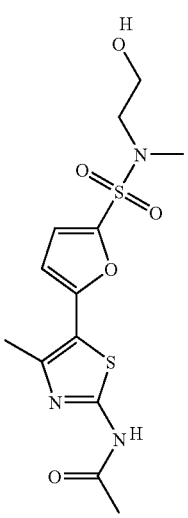

TABLE 1-continued
25
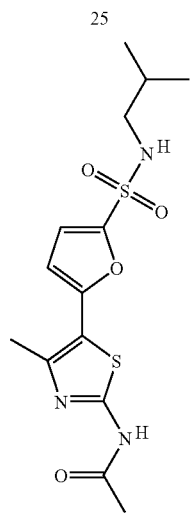
26
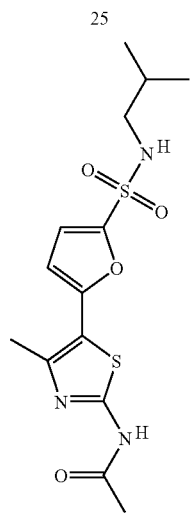
27
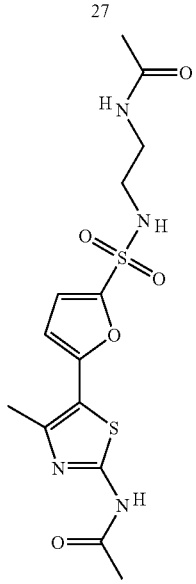
TABLE 1-continued
28
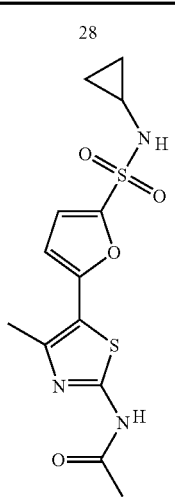
29
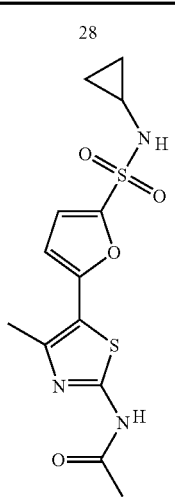
30
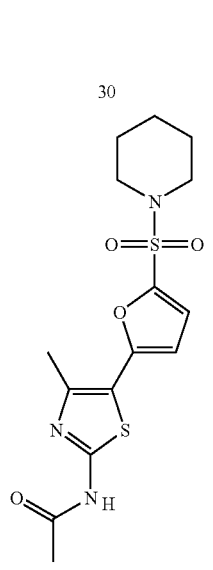

TABLE 1-continued
31
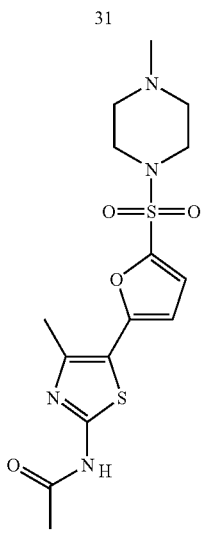
32
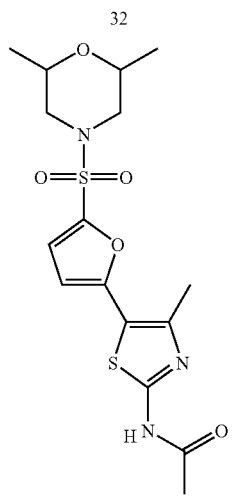
33
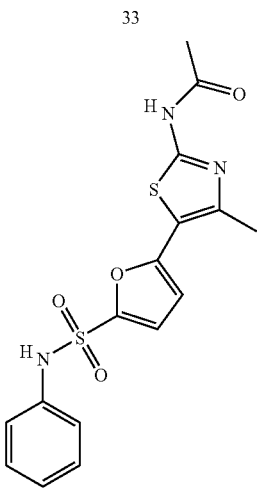
TABLE 1-continued
34
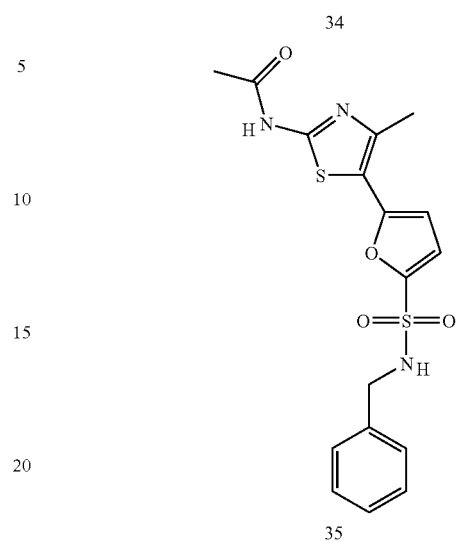
35
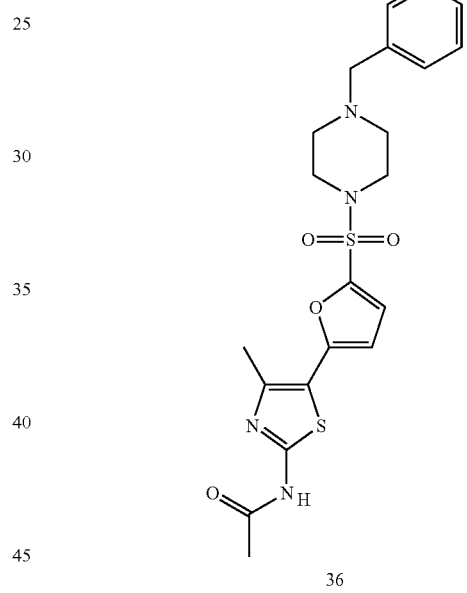
36
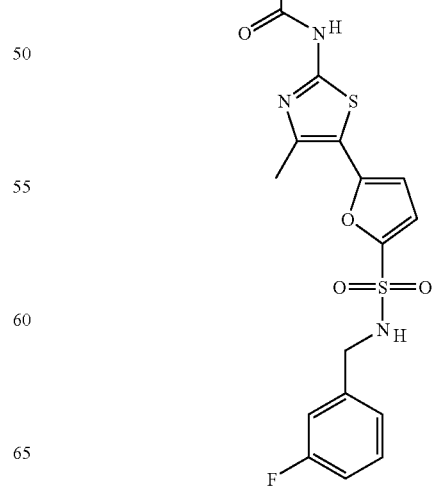

TABLE 1-continued
37
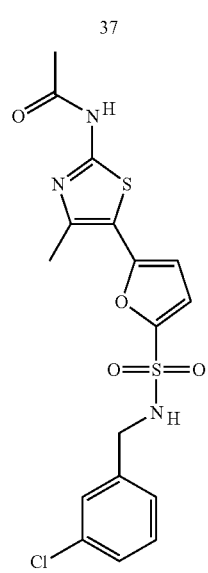
38
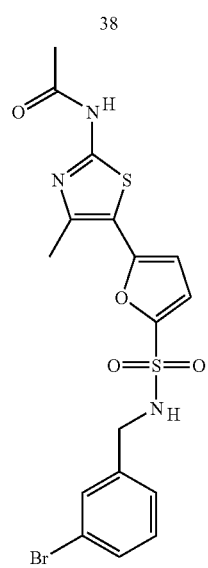
39
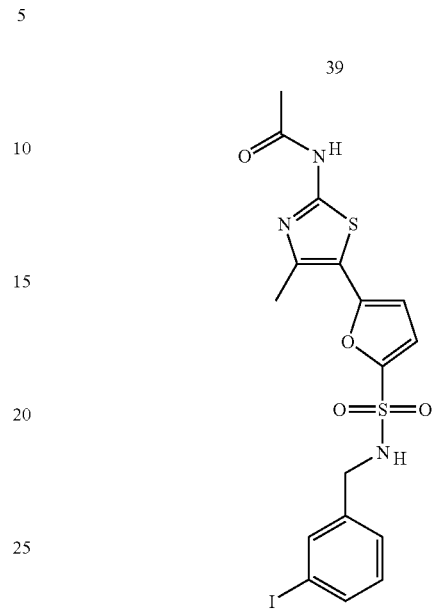
40
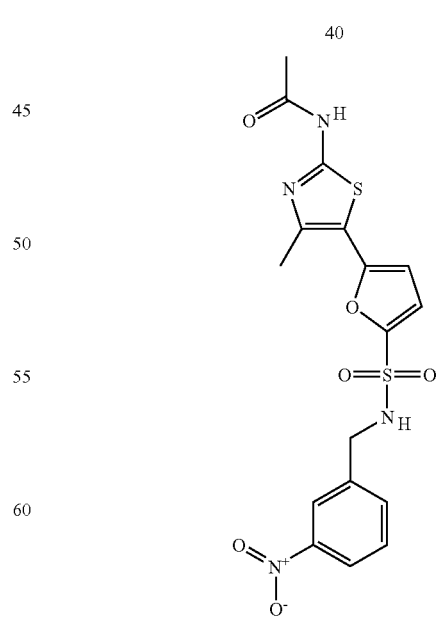

TABLE 1-continued
41
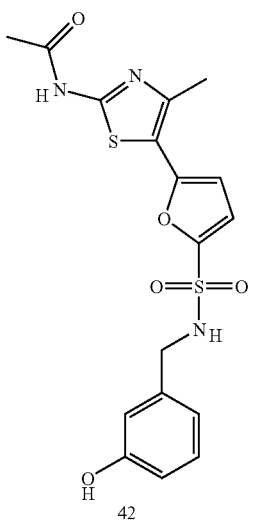
42
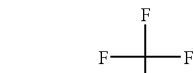
43
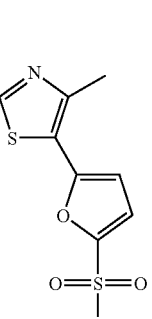
TABLE 1-continued
44
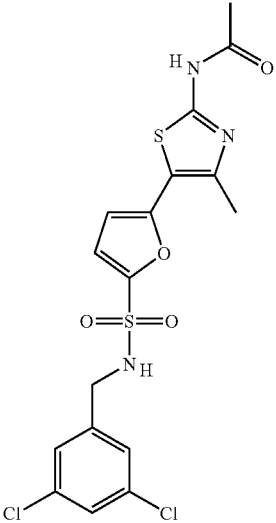
45
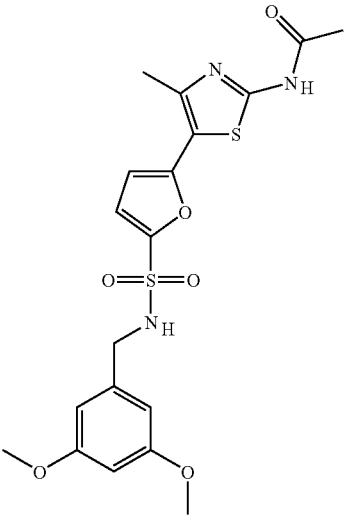
46
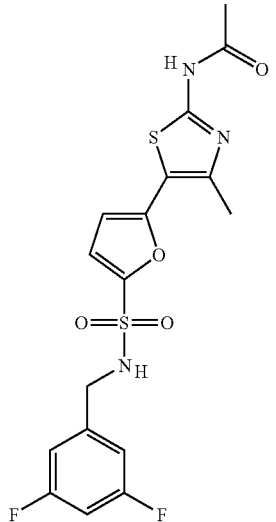

TABLE 1-continued
47
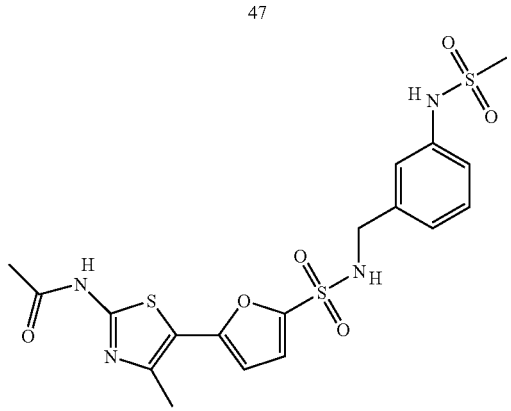
48
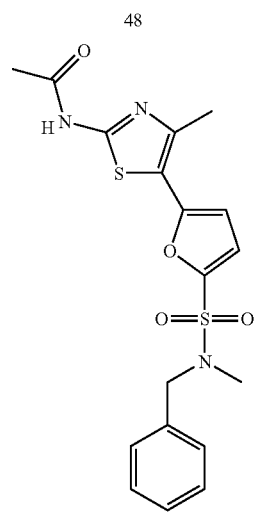
TABLE 2
49
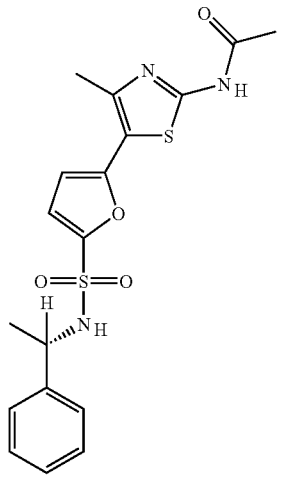
TABLE 2-continued
50
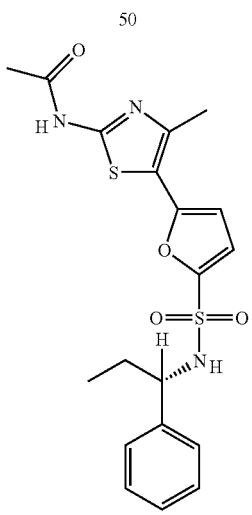
51
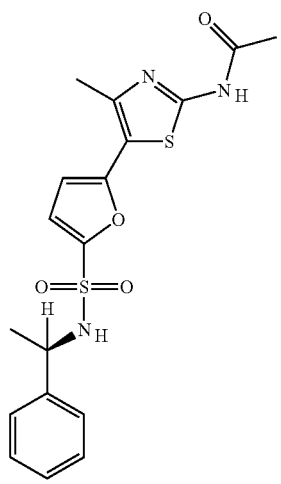
52
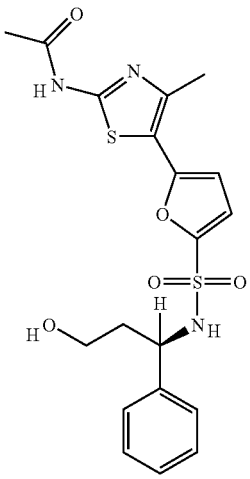

TABLE 2-continued
53
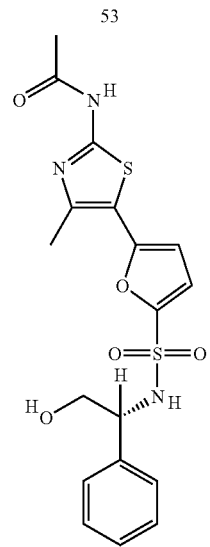
54
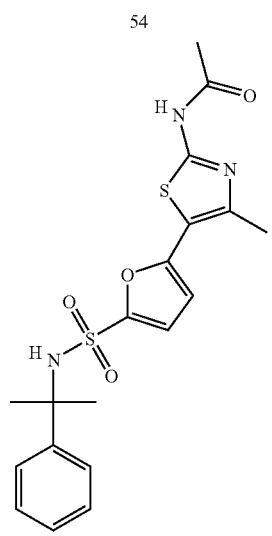
55
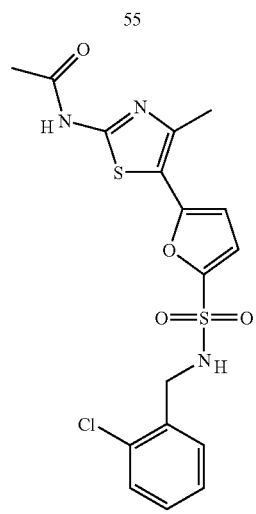
TABLE 2-continued
56
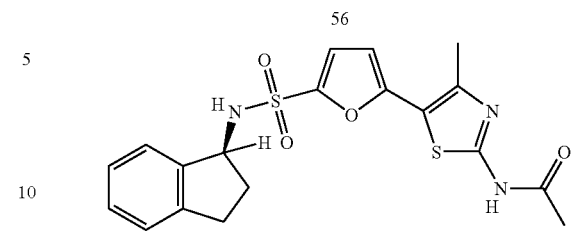
57
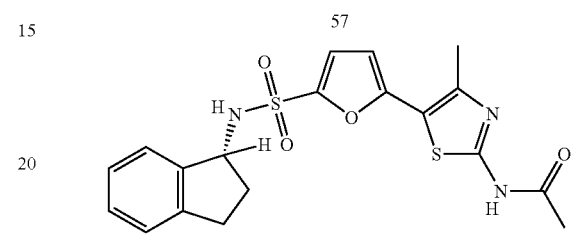
58
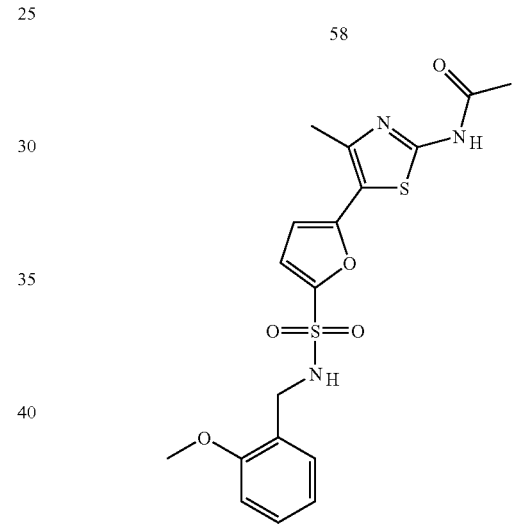
59
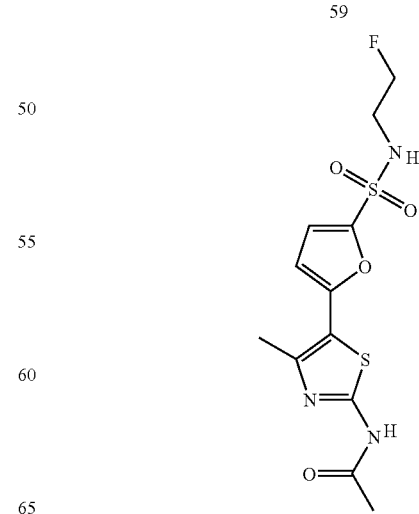

TABLE 2-continued
60
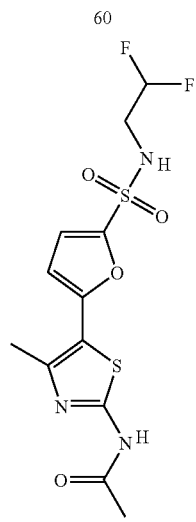
61
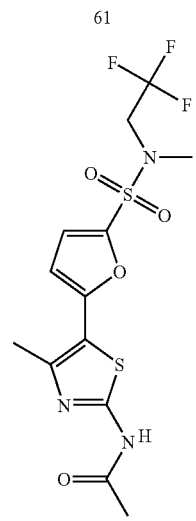
62
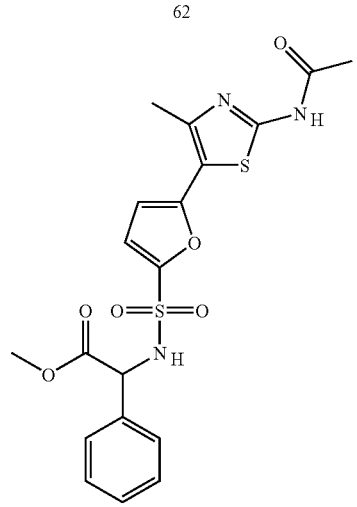
TABLE 2-continued
63
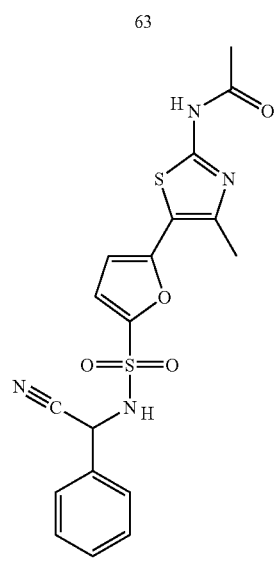
64
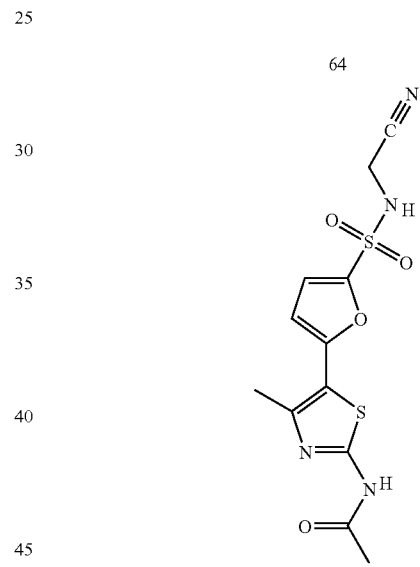
65
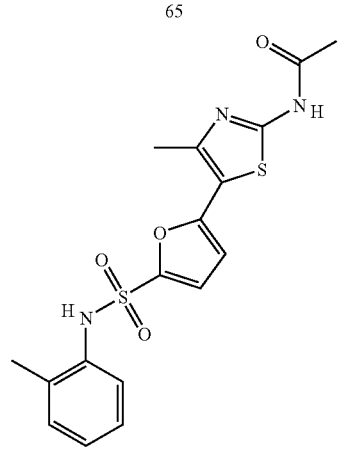

TABLE 2-continued
66
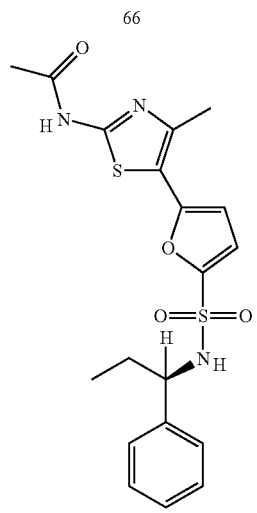
67
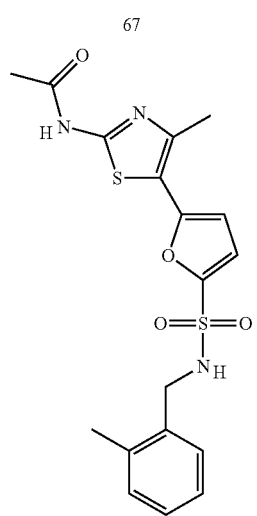
68
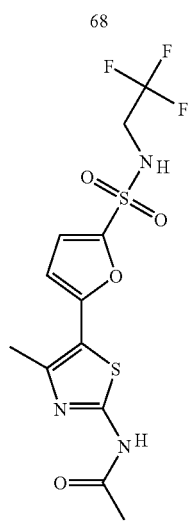
TABLE 2-continued
69
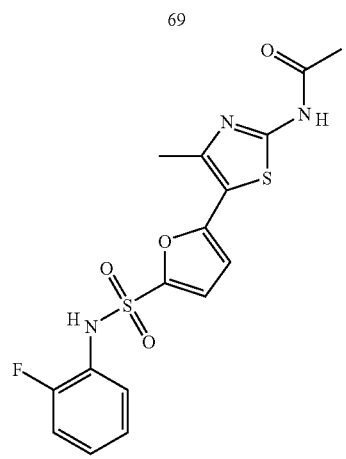
70
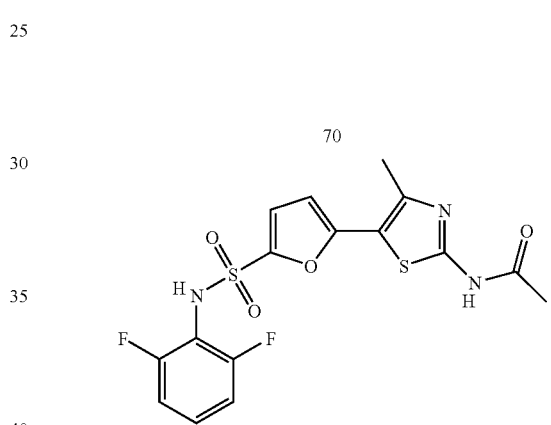
71
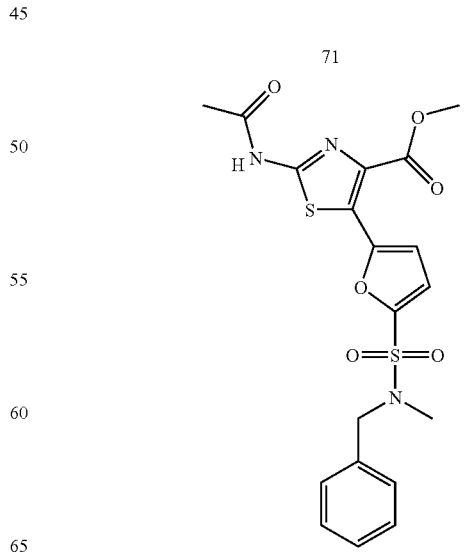

TABLE 2-continued

72

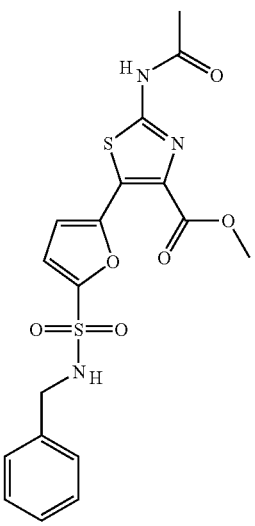

73

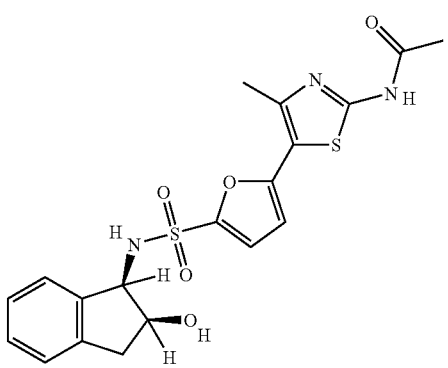

74

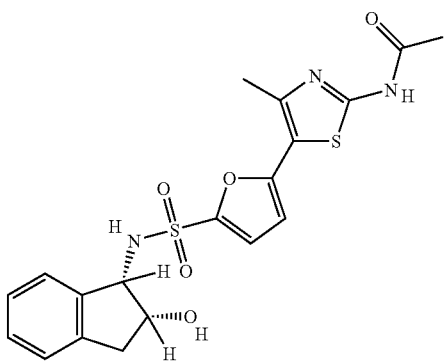

Uses, Formulation and Administration

Pharmaceutically Acceptable Compositions

In another embodiment, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a PI3K, particularly PI3Kγ, in a biological sample or in a patient. In another embodiment, the amount of compound in the compositions of this invention is such that is effective to measurably inhibit PI3Kα. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds or pharmaceutically acceptable salts thereof, as described herein, and further comprises a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitorily active metabolite or residue thereof" means that a metabolite or residue thereof is also an inhibitor of PI3K.

As used herein, the term "pharmaceutically acceptable salt" refers to those salts which are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly PI3K activity, between a sample comprising a compound of this invention and a PI3K and an equivalent sample comprising PI3K in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

In one embodiment, chemotherapeutic agents or other antiproliferative agents may be combined with the compounds of this invention to treat proliferative diseases and cancer. Chemotherapeutic drugs include but are not limited to alkylating drugs (mechlorethamine, chlorambucil, cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), biologic response modifiers (interferons, interleukins, and tumor necrosis factor (TNF), hormones (Tamoxifen, Leuprolide, Flutamide, and Megestrol), Gleevec™, adriamycin, dexamethasone, and cyclophosphamide. In a further embodiment, additional chemotherapeutic agents include Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: agents for treating Multiple Sclerosis (MS) such as beta interferon (e.g., Avonex® and Rebif®), Copaxone®, and mitoxantrone; treatments for asthma such as albuterol and Singulair®; anti-inflammatory agents such as NSAIDS, corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; agents for treating cardiovascular disease such as beta-blockers, ACE inhibitors, diuretics, nitrates, calcium channel blockers, and statins; agents for treating diabetes, including insulin, glitazones and sulfonyl ureas; and agents for treating blood disorders such as corticosteroids and anti-leukemic agents.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In one embodiment, the invention provides a method of inhibiting PI3K activity in a patient, comprising administering to said patient a compound or composition of the invention.

In another embodiment, the invention comprises a method of treating or lessening the severity of a PI3K-mediated condition or disease in a patient. The term "PI3K-mediated disease", as used herein means any disease or other deleterious condition in which PI3K, in particular PI3Kγ, is known to play a role. In another embodiment, a PI3K disease is one in which PI3Kα is known to play a role. In a further embodiment, the invention comprises a method of treating a PI3K-mediated disease. Such conditions include, without limitation, autoimmune diseases, inflammatory diseases, thrombolytic diseases, cancer, cardiovascular diseases, diabetes, allergic diseases, asthma and respiratory diseases.

In another embodiment, the invention provides a method of treating or lessening the severity of a disease of condition selected from cancer, autoimmune diseases, inflammatory diseases, cardiovascular diseases, diabetes, and allergic diseases or asthma, comprising administering to said patient a compound or composition of the invention.

In one embodiment, the invention provides a method of treating or lessening the severity of cancer. Examples of cancers that may be treated or ameliorated by a method of the invention include, without limitation, cancer of the breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system. The invention also provides a method of treating or lessening the severity of leukemias, including, without limitation, acute lymphocytic leukemia (ALL), chronic myelogenous leukemia (CML), multiple myeloma and lymphomas. In one embodiment, the invention provides a method of treating or lessening the severity of cancer selected from ovarian cancer, colon cancer, colorectal cancer, breast cancer, brain cancer and lung cancer.

In another embodiment, the invention provides a method of treating or lessening the severity of an autoimmune disease or disorder. Autoimmune diseases or disorders include, without limitation, rheumatoid arthritis, systemic lupus erythematosus (SLE), multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, Sjogren's syndrome and graft vs. host disease. In one embodiment, the autoimmune disease or disorder is rheumatoid arthritis, SLE or mutiple sclerosis.

In another embodiment, the invention provides a method of treating or lessening the severity of organ transplantation rejection.

In another embodiment, the invention provides a method of treating or lessening the severity of an inflammatory disease. Inflammatory diseases include, without limitation, chronic obstructive pulmonary disease (COPD), bronchitis, emphysema, farmer's lung and related diseases, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis. In one embodiment, the inflammatory disease is acute respiratory distress syndrome or lacrimal parotid gland syndrome.

In another embodiment, the invention provides a method of treating or lessening the severity of a cardiovascular disease. Cardiovascular diseases include, without limitation, atherosclerosis, pulmonary hypertension, deep venous thrombosis, stroke, myocardial infarction, myocardial contractility disorders, ischemia, thromboembolism, pulmonary embolism, acute arterial ischemia, peripheral thrombotic occlusions, coronary artery disease and acute coronary syndrome (ACS). In one embodiment, the cardiovascular disease is atherosclerosis, a myocardial contractility disorder or acute coronary syndrome.

In another embodiment, the invention provides a method of treating or lessening the severity of type II diabetes.

In another embodiment, the invention provides a method of treating or lessening the severity of allergic diseases or asthma. Examples of allergic diseases include, without limitation, perennial and seasonal allergic rhinitis, type I hypersensitivity reactions, atopic dermatitis, contact dermatitis, eczema, In a further embodiment, the invention provides a method of treating or lessening the severity of rheumatoid arthritis, SLE, multiple sclerosis, lacrimal parotid gland syndrome, COPD, pancreatitis, atherosclerosis, myocardial infarction, diabetes or cancer. In another embodiment, the disease or disorder is rheumatoid arthritis, SLE, atherosclerosis, multiple sclerosis or cancer. In another embodiment, the disease or disorder is rheumatoid arthritis, multiple sclerosis or SLE.

In a further embodiment, the method comprises the additional step of administering to said patient one or more additional therapeutic agents. Additional therapeutic agents include chemotherapeutic agents or other anti-proliferative agents, such as Gleevec™, adriamycin, dexamethasone, vincristine, cyclophosphamide, fluorouracil, topotecan, taxol, interferons, and platinum derivatives; agents for treating multiple sclerosis (MS) such as beta interferon (e.g., Avonex® and Rebif®), Copaxone®, and mitoxantrone; treatments for asthma such as albuterol and Singulair®; anti-inflammatory agents such as NSAIDS, corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; agents for treating cardiovascular disease such as beta-blockers, ACE inhibitors, diuretics, nitrates, calcium channel blockers, and statins; agents for treating diabetes, including insulin, glitazones and sulfonyl ureas; and agents for treating blood disorders such as corticosteroids and anti-leukemic agents. In one embodiment, said additional therapeutic agent is appropriate for the disease being treated and said additional therapeutic agent is administered together with said composition as a single dosage form or separately from said composition as part of a multiple dosage form. When these additional therapeutic agents are administered separately they may be administered to the patient prior to, sequentially with or following administration of the compositions of this invention.

In another embodiment, the invention provides a method of inhibiting PI3K activity in a biological sample, comprising contacting said biological sample with a compound or composition of the invention.

The term "biological sample", as used herein, means an ex vivo sample, and includes, without limitation, cell cultures or extracts thereof; tissue or organ samples or extracts thereof, biopsied material obtained from a mammal or extracts thereof; and blood, saliva, urine, feces, semen, tears, or other body fluids or extracts thereof.

Inhibition of PI3K activity, particularly PI3Kγ activity, in a biological sample is useful for a variety of purposes that are known to one of skill in the art. Examples of such purposes include, but are not limited to, biological specimen storage and biological assays.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention because, without wishing to be bound to a theory, a compound of the invention could prevent or decrease inflammation or unwanted cellular proliferation, Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

The invention also provides a method of screening a compound for the ability to inhibit phosphatidylinositol 3-kinase (PI3K) activity. The method comprises:

a) mixing the compound with PI3K, adenosine triphospate (ATP) and a phosphatidylininositol (PI) in a buffer in which PI3K is active to form a mixture;

b) incubating the mixture at a temperature and for a time sufficient for said PI3K to phosphorylate said PI;

c) measuring the amount of phosphorylated PI that is produced comprising:

i) adding a stop buffer to the mixture in step b) to form a stopped mixture;
 ii) transferring the quenched mixture to a glass fiber filter (GFF) or hydrophobic membrane;
 iii) washing the quenched mixture with a wash buffer; and
 iv) measuring the phosphorylated PI on the GFF or hydrophobic membrane; and d) determining whether said compound inhibits said PI3K.

Methodology for Synthesis and Characterization of Compounds

All references provided in the Examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

EXAMPLES

Example 1

Preparation of Compounds of the Invention

N-(5-bromo-4-methylthiazol-2-yl)cyclopropanecarboxamide

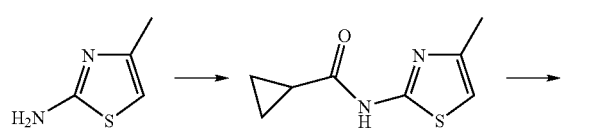

To a solution of 4-methylthiazol-2-amine (20.4 g) in pyridine (80 ml) under an ice bath was added dropwise cyclopropanecarbonyl chloride (19.7 ml) and the resulting reaction was stirred at room temperature (RT) overnight. A half volume of pyridine was removed using a rotary evaporator to afford a residue, to which water (100 ml) was added. Filtration, washing with water (3×100 ml) and drying under vacuum afforded N-(4-methylthiazol-2-yl)cyclopropanecarboxamide as a white solid (29.92 g).

To N-(4-methylthiazol-2-yl)cyclopropanecarboxamide (10.05 g) in acetic acid (100 ml) under an ice-water bath was added bromine (3.2 ml). After 30 min, water (100 ml) was added. Filtration, washing with water (3×) and drying under vacuum afforded N-(5-bromo-4-methylthiazol-2-yl)cyclopropanecarboxamide as a white solid (12.47 g). H NMR (500 MHz, CDCl$_3$) 2.39 (s, 3 H), 1.64-1.60 (m, 1 H), 1.27-1.24 (m, 2 H), 1.00-0.96 (m, 2 H) ppm; LC/MS: 261 (M+1)/2.91 min.

Ethyl 5-(2-(cyclopropanecarboxamido)-4-methylthiazol-5-yl)furan-2-carboxylate (Compound 1)

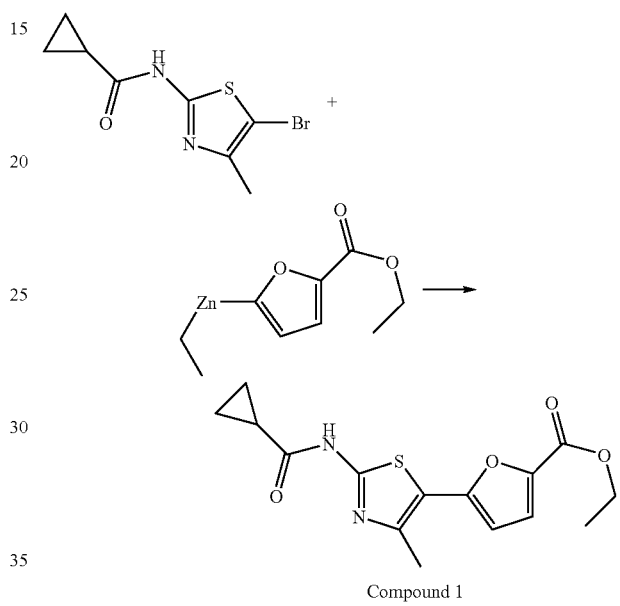

Compound 1

A solution of N-(5-bromo-4-methylthiazol-2-yl)cyclopropanecarboxamide (1.0 g), Pd$_2$dba$_3$ (70 mg), and tri-orthotolyl phosphine (300 mg) in 40 mL of THF was degassed via nitrogen bubbling for 2 hrs. To this solution was added 15 mL of a 2.0 M solution of (5-(ethoxycarbonyl)furan-2-yl)(ethyl) zinc (2 equiv) as a single portion. The reaction was warmed to 60° overnight under nitrogen. The reaction was quenched with 10 mL of methanol, concentrated to dryness and the residue suspended in methylene chloride, which was filtered. The filtrate was concentrated and he residue was purified via silica gel chromatography (CH$_2$Cl$_2$ to EtOAc) to yield 100 mg of compound 1 as a white solid.

N-(5-bromo-4-methylthiazol-2-yl)acetamide

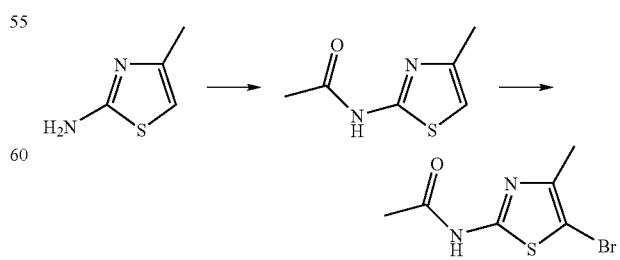

To a solution of 4-methylthiazol-2-amine (36.28 g) in pyridine (130 ml) under an ice bath was added dropwise acetyl chloride (30 ml) in 30 min. The resulting suspension was left at RT overnight. Most of the pyridine was removed under vacuum. To the residue was added water (500 ml) and the pH was adjusted to 7 by adding aqueous HCl. Extraction with ethyl acetate (3×400 ml), washing with brine, drying and concentration under a rotary evaporator gave a residue, which was washed with ether to generate pure N-(4-methylthiazol-2-yl)acetamide as a white solid (41.48 g).

To N-(4-methylthiazol-2-yl)acetamide (39.48 g) in acetic acid (200 ml) under a water-ice bath was added dropwise bromine (16 ml). After 2 h, water (500 ml) was added. Filtration, washing with water (3×) and drying gave N-(5-bromo-4-methylthiazol-2-yl) acetamide as off-white solid (52.13 g). H1-NMR (300 MHz, d6-DMSO) 12.27 (s, 1 H), 2.22 (s, 3 H), 2.13 (s, 3 H) ppm.

N-(5-(5-formylfuran-2-yl)-4-methylthiazol-2-yl)
acetamide

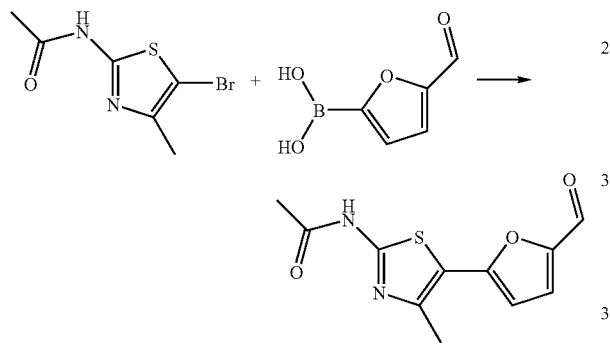

To a solution of 3.0 g of N-(5-bromo-4-methylthiazol-2-yl)acetamide in 50 mL of NMP was added 3.0 g of 5-formyl-furan-2-ylboronic acid. To the stirred solution was then added 300 mg of 1,1 bis-(diphenylphosphino)-ferrocene) palladium dichloride followed by 10 mL of saturated sodium bicarbonate. The resulting biphasic mixture was irradiated at 150° C. in a microwave for 20 min. The resulting mixture was poured into 200 mL of water and filtered. The filtrate was extracted with ether and the ether layers were combined, dried over sodium sulfate and concentrated. The resulting oil was precipitated with methylene chloride and filtered, yielding 1.2 g of N-(5-(5-formylfuran-2-yl)-4-methylthiazol-2-yl)acetamide as an orange solid which was used without further purification. LC/MS: 251.07 (M+H)/2.18 min.

5-(2-acetamido-4-methylthiazol-5-yl)furan-2-car-
boxylic acid

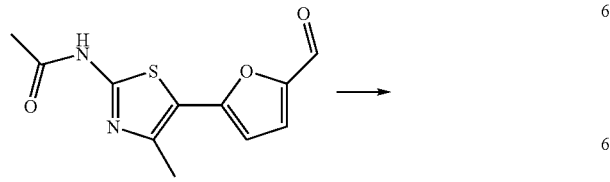

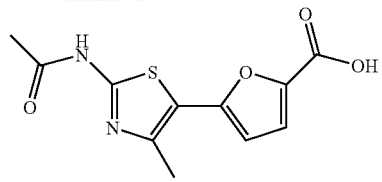

To a solution of 1.2 g of N-(5-(5-formylfuran-2-yl)-4-methylthiazol-2-yl)acetamide in 100 mL of tert-butanol was added 5 mL of water and 20 mL of 2N monobasic sodium phosphate. The resulting suspension was cooled to 0° C. while being stirred. To the chilled suspension was added 20 mL of a 2M solution of 2-methyl-2-butene in THF followed by 3 g of sodium chlorite in 10 mL of water. The reaction was allowed to warm to room temperature overnight and the upper organic layer was separated and dried over sodium sulfate and used as is in the subsequent reactions. LC/MS: 267.04 (M+H)/2.04 min.

(R)-5-(2-acetamido-4-methylthiazol-5-yl)-N-(2-hy-
droxy-1-phenylethyl)furan-2-carboxamide (Com-
pound 10)

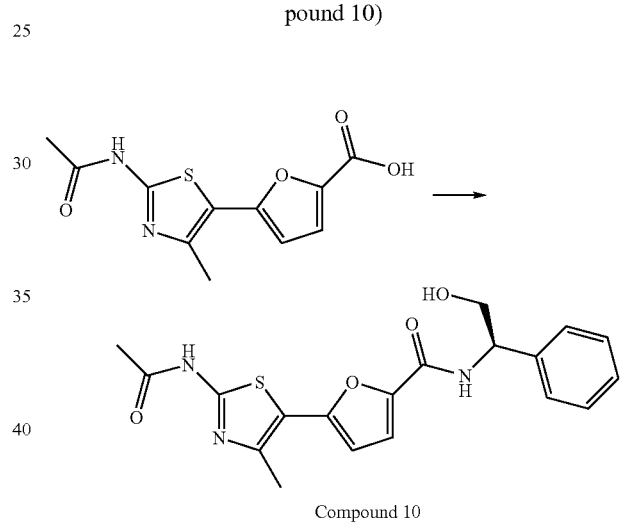

Compound 10

To 5 mL of the crude 4.49 millimolar solution of 5-(2-acetamido-4-methylthiazol-5-yl)furan-2-carboxylic acid was added 200 mg of TBTU and 1 mL of Hunig's base. To the stirred reaction mixture was then added 200 mg of S-phenylglycinol. The reaction was allowed to stir overnight and was then concentrated to dryness and dissolved in 1 mL of DMSO and filtered. The filtrate was purified via reverse phase chromatography to yield 4.1 mg of (R)-5-(2-acetamido-4-methylthiazol-5-yl)-N-(2-hydroxy-1-phenylethyl)furan-2-carboxamide as a white solid. LC/MS: 386.2 (M+H)/2.0 min.

Compounds 2-9 and 11-18 were prepared in an analogous fashion.

N-(5-(furan-2-yl)-4-methylthiazol-2-yl)acetamide

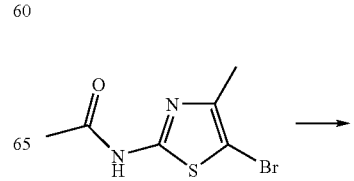

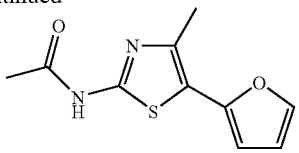

A mixture of N-(5-bromo-4-methylthiazol-2-yl)acetamide (4 g), furan-2-yl-2-boronic acid (4.22 g), tetrakis(triphenylphosphine)palladium (1.8 g) and 2 N sodium carbonate (36 ml) in DME (60 ml) was stirred at 95° C. for 18 h. After cooling, water (100 ml) was added. Extraction with ethyl acetate (3×80 ml), drying, concentration and purification (SiO$_2$, 0 to 100% ethyl acetate in hexane) gave pure N-(5-(furan-2-yl)-4-methylthiazol-2-yl)acetamide (2.95 g).

5-(2-Acetamido-4-methylthiazol-5-yl)furan-2-sulfonyl chloride

To N-(5-(furan-2-yl)-4-methylthiazol-2-yl)acetamide (0.443 g) under an ice-salt bath was added sulfurochloridoic acid (ClSO$_3$H, 5 ml). After 30 min, the reaction was poured into crushed ice (150 g). Extraction with dichloromethane (3×30 ml), drying and concentration gave 5-(2-acetamido-4-methylthiazol-5-yl)furan-2-sulfonyl chloride (0.359 g) that was used directly for next step.

Preparation of Compounds 19-74

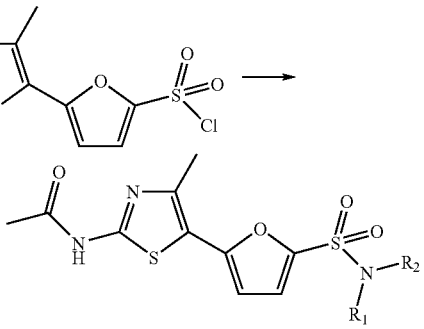

VRTs

To a solution of 20 mg (0.66 mmol) 5-(2-acetamido-4-methylthiazol-5-yl)furan-2-sulfonyl chloride in 1 mL dry chloroform was added 0.28 mL (2 mmol, 3 equivalents) triethylamine with stirring to give a colorless solution. To this was added was the appropriate amine (NR$^1$R$^2$; 1.5 equivalent). The resulting reaction was stirred at RT over night. Evaporation gave a residue that was purified by HPLC to give the sulfonamides.

Example 2

Analytical Results

Table 3 below depicts exemplary $^1$H-NMR data (NMR) and liquid chromatographic mass spectral data, reported as mass plus proton (M+H), as determined by electrospray, and retention time (RT) for certain compounds of the present invention, wherein compound numbers in Table 3 correspond to the compounds depicted in Tables 1 and 2 (empty cells in the NMR column indicate that results were not available):

TABLE 3

| Cpd # | M + H | RT | NMR |
|---|---|---|---|
| 1 | 320.9 | 3.1 | (500 MHz, CDCl3) 7.16-7.15 (m, H), 6.39 (d, J = 3.6 Hz, H), 4.29 (q, J = 7.1 Hz, 2H), 2.50 (s, 3H), 1.58-1.53 (m, 1H), 1.31 (t, J = 7.1 Hz, 3H), 1.20-1.11 (m, 2H), 0.93-0.87 (m, 2H) ppm |
| 2 | 360.2 | 2.23 | |
| 3 | 424.1 | 2.86 | |
| 4 | 474 | 2.71 | |
| 5 | 352.1 | 2.1 | |
| 6 | 348.2 | 2.4 | |
| 7 | 349.2 | 1.7 | |
| 8 | 424.2 | 2.4 | |
| 9 | 319.1 | 1.8 | |
| 10 | 386.2 | 2 | |
| 11 | 334.2 | 2.2 | |
| 12 | 364.2 | 2 | |
| 13 | 428.2 | 2.8 | |
| 14 | 336.2 | 1.5 | |
| 15 | 403.3 | 1.7 | |
| 16 | 435.2 | 2.6 | |
| 17 | 350.2 | 1.7 | |
| 18 | 424.1 | 2.6 | |
| 19 | 302.2 | 1.9 | |
| 20 | 316.2 | 2.01 | (300 MHz, DMSO-d6) 12.33 (s, 1H), 7.92 (q, J = 4.9 Hz, 9.6 Hz, 1H), 7.20 (d, J = 3.5 Hz, 1H), 6.77 (d, J = 3.6 Hz, 1H), 2.54 (d, J = 4.9 Hz, 3H), 2.45 (s, 3H), 2.16 (s, 3H) |

TABLE 3-continued

| Cpd # | M + H | RT | NMR |
|---|---|---|---|
| 21 | 330.2 | 2.25 | (300 MHz, DMSO-d6) 12.35 (s, 1H), 7.30 (d, J = 6.6 Hz, 1H), 6.83 (d, 6.4 Hz, 1H), 2.77 (s, 6H), 2.47 (s, 3H), 2.17 (s, 3H) |
| 22 | 346.2 | 1.72 | (300 MHz, DMSO-d6) 12.33 (s, 1H), 8.09 (t, J = 5.6 Hz, 1H), 7.17 (d, J = 3.4 Hz, 1H), 6.75 (d, J = 3.5 Hz, 1H), 3.38 (t, J = 6.8 Hz, 3H), 2.94 (q, J = 6.0 Hz, 12.3 Hz, 2H), 2.45 (s, 3H), 2.16 (s, 3H) |
| 23 | 360.4 | 2.05 | (300 MHz, DMSO-d6) 12.33 (s, 1H), 8.21 (t, J = 5.7 Hz, 1H), 7.16 (d, J = 3.6 Hz, 1H), 6.75 (d, J = 3.7 Hz, 1H), 3.32 (t, J = 5.7 Hz, 2H), 3.17 (s, 3H), 3.06 (q, J = 6 Hz, 11.3 Hz, 2H), 2.45 (s, 3H), 2.16 (s, 3H) |
| 24 | 360.4 | 1.88 | (300 MHz, DMSO-d6) 12.34 (s, 1H), 7.26 (d, J = 3.8 Hz, 1H), 6.80 (d, J = 3.6 Hz, 1H), 3.54 (t, J = 5.7 Hz, 2H), 3.17 (J = 5.8 Hz, 2H), 2.86 (s, 3H), 2.46 (s, 3H), 2.16 (s, 3H) |
| 25 | 358.5 | 2.52 | (300 MHz, DMSO-d6) 12.33 (s, 1H), 8.11 (t, J = 5.9 Hz, 1H), 7.16 (d, J = 4.0 Hz, 1H), 6.75 (d, J = 3.8 Hz, 1H), 2.71 (t, J = 6.4 Hz, 2H), 2.45 (s, 3H), 2.16 (s, 3H), 1.64 (m, 1H), 0.81 (d, J = 10.6 Hz, 6H) |
| 26 | 355.4 | 2.02 | |
| 27 | 387.4 | 1.71 | (300 MHz, DMSO-d6) 12.33 (s, 1H), 8.15 (t, J = 5.5 Hz, 1H), 7.87 (t, J = 5.6 Hz, 1H), 7.18 (d, J = 3.4 Hz, 1H), 6.76 (d, J = 3.4 Hz, 1H), 3.07 (m, 2H), 2.91 (m, 2H), 2.45 (s, 3H), 2.16 (3H), 1.75 (s, 3H) |
| 28 | 342.2 | 2.22 | (300 MHz, DMSO-d6) 12.34 (s, 1H), 8.37 (s, 1H), 7.22 (d, J = 3.6 Hz, 1H), 6.78 (d, J = 3.5 Hz, 1H), 2.45 (s, 3H), 2.32 (m, 1H), 2.17 (s, 3H), 0.54 (m, 2H), 0.39 (m, 2H) |
| 29 | 370.4 | 2.53 | (300 MHz, DMSO-d6) 12.33 (s, 1H), 8.13 (d, J = 7.2 Hz, 1H), 7.15 (d, J = 3.5, 1H), 6.75 (d, J = 3.5 Hz, 1H), 3.54 (m, 1H), 2.45 (s, 3H), 2.45 (s, 3H), 2.16 (s, 3H), 1.65 (m, 2H), 1.56 (m, 2H), 1.37 (m, 4) |
| 30 | 370.4 | 2.71 | |
| 31 | 385.5 | 1.82 | (300 MHz, DMSO-d6) 12.34 (s, 1H), 9.51 (m, 1H), 7.44 (d, J = 3.6 Hz, 1H), 6.92 (d, J = 3.5 Hz, 1H), 3.54 (m, 3H), 3.19 (s, 4H), 2.82 (m, 4H), 2.17 (s, 3H) |
| 32 | 400.5 | 2.61 | |
| 33 | 378.4 | 2.58 | |
| 34 | 392.4 | 2.61 | |
| 35 | 461.5 | 2.87 | |
| 36 | 410.1 | 2.45 | |
| 37 | 426.1 | 2.67 | |
| 38 | 472 | 2.7 | |
| 39 | 518 | 2.74 | |
| 40 | 437.1 | 2.37 | |
| 41 | 408.1 | 2.02 | |
| 42 | 460.1 | 2.76 | |
| 43 | 476.1 | 2.82 | |
| 44 | 460 | 2.83 | |
| 45 | 452.2 | 2.48 | |
| 46 | 428.1 | 2.61 | |
| 47 | 485.1 | 2.2 | |
| 48 | 406.1 | 2.82 | |
| 49 | 406.10 | 2.60 | |
| 50 | 420.10 | 2.70 | |
| 51 | 406.10 | 2.60 | |
| 52 | 436.10 | 2.10 | |
| 53 | 422.10 | 2.10 | |
| 54 | 420.10 | 2.70 | |
| 55 | 426.00 | 2.70 | |
| 56 | 418.10 | 2.70 | |
| 57 | 418.10 | 2.70 | |
| 58 | 422.10 | 2.60 | |
| 59 | 348.10 | 2.10 | |
| 60 | 366.00 | 2.20 | |
| 61 | 398.10 | 2.90 | (300 MHz, CDCl3) 7.14 (d, J = 3.6 Hz, 1H), 6.48 (d, J = 3.6 Hz, 1H), 3.91-3.77 (m, 2H), 3.06 (s, 3H), 2.52 (s, 3H), 2.29 (s, 3H) |
| 62 | 450.10 | 2.50 | |
| 63 | 417.10 | 2.50 | |
| 64 | 341.10 | 2.00 | |
| 65 | 392.10 | 2.60 | |
| 66 | 420.10 | 2.80 | |
| 67 | 406.00 | 2.70 | |
| 68 | 384.20 | 2.63 | (300 MHz, CDCl3) 7.13 (d, J = 3.6 Hz, 1H), 6.46 (d, J = 3.6 Hz, 1H), 3.77 (q, J = 8.7 Hz, 2H), 2.48 (s, 3H), 2.28 (s, 3H) |
| 69 | 396.00 | 2.60 | |
| 70 | 414.00 | 2.50 | |
| 71 | 450.00 | 2.80 | |

TABLE 3-continued

| Cpd # | M + H | RT | NMR |
|---|---|---|---|
| 72 | 436.00 | 2.50 | |
| 73 | 434.00 | 2.40 | |
| 74 | 434.00 | 2.40 | |

Example 3

PI3K Inhibition Assay

Compounds were screened for their ability to inhibit PI3Kγ using one of the assays below.

Protocol A

To each well of a 96 well polystyrene plate [Corning, Costar Item No. 3696], was added 1.5 μl of a compound of the invention (at various concentrations) along with 28.5 W of kinase buffer [50 mM HEPES (pH 7.4), 5 mM DTT, 5 mM MgCl$_2$ and 50 mM NaCl] containing 137 μM phosphatidylinositol(4,5) bisphosphate diC8 [PI(4,5)P$_2$; Echelon Biosciences, Cat. No. P-4508] and 158 nM PI3Kγ. After mixing, 30 μl of kinase buffer containing 80 μM ATP was added to start the reaction. Final substrate concentrations in the assay were 50 mM HEPES (pH 7.4), 5 mM DTT, 5 mM MgCl$_2$, 50 mM NaCl, 40 μM ATP (200 μCi/μmole ATP), 65 μM PI(4,5)P$_2$ and 75 nM PI3Kγ. After 20 minutes at room temperature (25° C.), the reaction was stopped with 30 μl of kinase buffer containing 150 mM EDTA and 1.5 M ammonium sulfate.

Each well of a 96 well hydrophobic membrane filter plate [Millipore, 0.45 μm hydrophobic membrane, Cat. No. MSIP N4B] was washed with 100 μL wash buffer [50 mM HEPES (pH 7.4), 5 mM DTT, 5 mM MgCl$_2$, 50 mM NaCl, 5 mM EDTA and 0.5 M ammonium sulfate]. 60 μL of the stopped assay was transferred to each well of the filter plate and soaked for 30 minutes. After washing each well three times with 200 μL, wash buffer, 50 μl of scintillation fluid was added. The filter plate was allowed to stand overnight prior to determining $^{33}$P incorporation on a Perkin-Elmer Microbeta Trilux™ liquid scintillation counter and luminescence counter.

Protocol B

To each well of a 96 well polystyrene plate [Corning Costar Item No. 3795], 61 μL of Reaction Mix [55 mM HEPES pH 7.5, 11 mM MgCl$_2$, 27 mM NaCl, 5.5 mM DTT, 0.11 mg/mL BSA, 51 μM phosphatidylinositol(4,5)bisphosphate diC16 (PI(4,5)P$_2$; Avanti Polar Lipids, Cat. No. 840046P) and 18 nM PI3Kγ] was added. Separately, ten 2.5-fold serial dilutions of compounds of the invention were prepared in 100% DMSO with the last two wells reserved for no inhibitor controls (enzyme+no compound and no enzyme control+no compound). 1 μL it of compound or DMSO alone was added by 12-channel hand pipet and incubated for 10 minutes at room temperature (25° C.). To initiate the reaction, 5 μl of ATP Mix [49 mM HEPES pH 7.5 and 1340 $^{33}$P-ATP was added and allowed to incubate for 30 min. at 25° C. Final concentrations of the reaction were 50 mM HEPES 7.5, 10 mM MgCl$_2$, 25 mM NaCl, 5 mM DTT, 0.1 mg/mL BSA, 46 μM PI(4,5)P$_2$, 16.6 nM PI3Kγ, and 100 μM ATP. Final inhibitor concentrations ranged from 10 μM to 1 nM.

After incubation, 60 μL of the reaction was quenched by transferring to 504 of 20% TCA/Water in each well of a 96 well glass fiber filter plate [Millipore Cat. No. MAFBN0B50]. The plate was dried by vacuum and then washed five times in a Bio-Tek Instruments ELX-405 Auto Plate Washer with 150 μL of 5% TCA/Water. 50 μL of scintillation fluid was added to each well and the plate was read immediately on a Perkin-Elmer TopCount™ NXT liquid scintillation counter.

Inhibition data was background subtracted (no enzyme control+no inhibitor control) and fit to the competitive tight binding K$_i$ equation described by Morrison and Stone. [J. F. Morrison and S. R. Stone, Comments Mol. Cell. Biophys. 2 (1985) 347-368].

Table 4 depicts enzyme inhibition data (KO for certain exemplary compounds. Compound numbers in Table 4 correspond to those compounds depicted in Tables 1 and 2. In Table 4, "A" represents a K$_i$ of less than 0.1 μM, "B" represents a K$_i$ of between 0.1 and ≦1.0 μM, and "C" represents a K$_i$ of >1.0 μM and less than 5.0 μM. If there was more than one result for a given compound, the average K$_i$ was provided. Compound 1 was assessed by Protocol A; all other compounds were assessed by Protocol B.

TABLE 4

| Cpd # | PI3Kγ |
|---|---|
| 1 | C |
| 2 | B |
| 3 | C |
| 4 | C |
| 5 | B |
| 6 | B |
| 7 | C |
| 8 | B |
| 9 | B |
| 10 | B |
| 11 | B |
| 12 | B |
| 13 | B |
| 14 | B |
| 15 | C |
| 16 | B |
| 17 | B |
| 18 | B |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | B |
| 44 | B |
| 45 | B |

TABLE 4-continued

| Cpd # | PI3Kγ |
|---|---|
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | B |
| 71 | C |
| 72 | B |
| 73 | A |
| 74 | A |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I

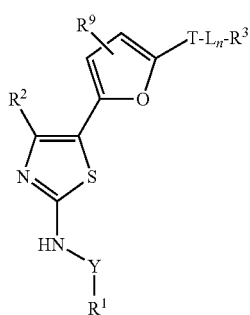

I or a pharmaceutically acceptable salt thereof, wherein:
Y is —C(O)— or a bond;
$R^1$ is a $C_{1-6}$ aliphatic, wherein up to three methylene units are replaced by —NH—, —$NR^{11}$—, —O—, —S—, —$CO_2$—, —OC(O)—, —C(O)CO—, —C(O)—, —C(O)O—, —C(O)NH—, —C(O)$NR^{11}$—, —NC(=N—CN)N, —NHCO—, —$NR^{11}$CO—, —NHC(O)O—, —$NR^{11}$C(O)O—, —$SO_2$NH—, —$SO_2NR^{11}$—, —$NHSO_2$—, —$NR^{11}SO_2$—, $SO_2$—, —NHC(O)NH—, —$NR^{11}$C(O)NH—, —NHC(O)$NR^{11}$—, —$NR^{11}$C(O)$NR^{11}$—, —OC(O)NH—, —OC(O)$NR^{11}$—, —$NHSO_2$NH—, —$NR^{11}SO_2$NH—, —$NHSO_2NR^{11}$—, —$NR^{11}SO_2NR^{11}$—, —SO—, or —$SO_2$—; a $C_{3-10}$ monocyclic or bicyclic cycloaliphatic; a $C_{6-10}$ monocyclic or bicyclic aryl; a 5-10 membered monocyclic or bicyclic heteroaryl; or a 5-10 membered monocyclic or bicyclic heterocyclyl; wherein $R^1$ is optionally substituted with 1-6 occurrences of $J^{R1}$;
each $R^{11}$ is independently selected from $C_{1-6}$ aliphatic, $C_{3-10}$ monocyclic or bicyclic cycloaliphatic, $C_{6-10}$ monocyclic or bicyclic aryl, 5-10 membered monocyclic or bicyclic heteroaryl, or 5-10 membered monocyclic or bicyclic heterocyclyl; or two $R^{11}$ groups, on the same substituent or different substituents, together with the atom(s) to which each $R^{11}$ group is bound, form a 3-8 membered heterocyclyl;
each $J^{R1}$ is independently selected from halogen, OH, OR, $NO_2$, $NH_2$, NHR, $NR_2$, SH, SR, CN, C(O)$NH_2$, C(O)NHR, C(O)$NR_2$, C(O)OH, C(O)OR, NHC(O)H, NHC(O)R, NRC(O)H, NRC(O)R, NHC(O)OH, NHC(O)OR, NRC(O)OH, NRC(O)OR, or R; or two $J^{R1}$, together with the carbon(s) to which they are attached, form a cyclopropyl ring or C=O;
each R is independently selected from a $C_{1-4}$ aliphatic or $C_{3-4}$ cycloaliphatic optionally substituted with 1-4 occurrences of halogen, OH, $NO_2$, $NH_2$, SH or CN;
$R^2$ is H, a $C_{1-6}$ aliphatic, $C_{3-6}$ cycloaliphatic, halogen, OH, OR, $NO_2$, $NH_2$, NHR, $NR_2$, SH, SR, CN, C(O)$NH_2$, C(O)NHR, C(O)$NR_2$, C(O)OH, C(O)OR, NHC(O)H, NHC(O)R, NRC(O)H, NRC(O)R, NHC(O)OH, NHC(O)OR, NRC(O)OH, NRC(O)OR, or R; wherein said $C_{1-6}$ aliphatic or $C_{3-6}$ cycloaliphatic is optionally substituted with 1-4 occurrences of $J^{R2}$;
each $J^{R2}$ is independently selected from halogen, OH, OR, $NO_2$, $NH_2$, NHR, $NR_2$, SH, SR, CN, C(O)$NH_2$, C(O)NHR, C(O)$NR_2$, C(O)OH, C(O)OR, NHC(O)H, NHC(O)R, NRC(O)H, NRC(O)R, NHC(O)OH, NHC(O)OR, NRC(O)OH, NRC(O)OR, or R; or two $J^{R2}$, together with the carbon(s) to which they are attached, form a cyclopropyl ring or C=O;
T is —$SO_2NR^4$—, —$CONR^4$— or —C(O)O—;
$R^4$ is H or a $C_{1-6}$ aliphatic or $C_{3-7}$ cycloaliphatic optionally substituted with 1-6 occurrences of $J^{R4}$;
each $J^{R4}$ is independently selected from halogen, OH, OR', $NO_2$, $NH_2$, NHR', $NR'_2$, SH, SR', CN, 5-6 membered aryl or heteroaryl, or R'; or two $J^{R4}$, together with the carbon(s) to which they are attached, form a cyclopropyl ring or C=O;
each R' is independently selected from a $C_{1-6}$ aliphatic or $C_{3-7}$ cycloaliphatic optionally substituted with 1-6 occurrences of halogen, OH, $NO_2$, $NH_2$, SH or CN;
b is 0 or 1;
L is a $C_{1-6}$ aliphatic wherein up to three methylene units are replaced by —NH—, —$NR^5$—, —O—, —S—, —$CO_2$—, —OC(O)—, —C(O)CO—, —C(O)—, —C(O)NH—, —C(O)$NR^5$—, —NC(=N—CN)N, —NHCO—, —$NR^5$CO—, —NHC(O)O—, —$NR^5$C(O)O—, —$SO_2$NH—, —$SO_2NR^5$—, —$NHSO_2$—, —$NR^5SO_2$—, —NHC(O)NH—, —$NR^5$C(O)NH—, —NHC(O)$NR^5$—, —$NR^5$C(O)$NR^5$—, —OC(O)NH—, —OC(O)$NR^5$—, —$NHSO_2$NH—, —$NR^5SO_2$NH—, —$NHSO_2NR^5$—, —$NR^5SO_2NR^5$—, —SO—, or —$SO_2$—, wherein L is optionally substituted with 1-4 occurrences of $R^6$;
each $R^5$ is independently selected from $C_{1-6}$ aliphatic, $C_{3-10}$ monocyclic or bicyclic cycloaliphatic, $C_{6-10}$ monocyclic or bicyclic aryl, 5-10 membered monocyclic or bicyclic heteroaryl, or 5-10 membered monocyclic or bicyclic heterocyclyl; or two $R^5$ groups, on the same substituent or different substituents, together with the atom(s) to which each R⁵ group is bound, form a 3-8 membered heterocyclyl;

each R⁶ is independently selected from halogen, OH, OR', NO₂, NH₂, NHR', NR'₂, SH, SR', CN, or R'; or two R⁶, together with the carbon(s) to which they are attached, form a cyclopropyl ring or C=O;

n is 0 or 1;

R³ is H or an optionally substituted group selected from a $C_{1-6}$ aliphatic, a $C_{3-10}$ monocyclic or bicyclic cycloaliphatic, a $C_{6-10}$ monocyclic or bicyclic aryl, a 5-10 membered monocyclic or bicyclic heteroaryl, or a 5-10 membered monocyclic or bicyclic heterocyclyl, wherein R³ is optionally substituted with 1-6 occurrences of $J^{R3}$; or R³ and R⁴, together with the nitrogen to which R⁴ is attached, form a 5-10 membered monocyclic or bicyclic heterocyclyl or heteroaryl, wherein n is 0 and said heterocyclyl or heteroaryl is optionally substituted with 1-6 occurrences of $J^{R3}$;

each $J^{R3}$ is independently selected from —(U)$_m$—X;

U is a $C_1$ aliphatic, wherein up to two methylene units are optionally and independently replaced by $G^U$ and wherein U is optionally substituted with 1-4 $J^u$;

$G^U$ is —NH—, —NR⁷—, —O—, —S—, —CO₂—, —OC(O)—, —C(O)CO—, —C(O)—, —C(O)NH—, —C(O)NR⁷—, —NC(=N—CN)N—, —NHCO—, —NR⁷CO—, —NHC(O)O—, —NR⁷C(O )O—, —SO₂NH—, —SO₂NR⁷—, —NHSO₂—, —NR⁷SO₂—, —NHC(O)NH—, —NR⁷C(O)NH—, —NHC(O)NR⁷—, —NR⁷C(O)NR⁷—, —OC(O)NH—, —OC(O)NR⁷—, —NHSO₂NH—, —NR⁷SO₂NH—, —NHSO₂NR⁷—, —NR⁷SO₂NR⁷—, —SO—, or —SO₂—;

R⁷ is $C_{1-6}$ aliphatic or $C_{3-7}$ cycloaliphatic optionally substituted with 1-6 occurrences of halogen, OH, NO₂, NH₂, SH or CN;

m is 0 or 1;

each $J^U$ is independently selected from halogen, OH, OR', NO₂, NH₂, NHR', NR'₂, SH, SR', CN, or R'; or two $J^U$, together with the carbon(s) to which they are attached, form a cyclopropyl ring or C=O;

X is H, halogen, OH, OR, NO₂, NH₂, NHR, NR₂, SH, SR, CN, C(O)NH₂, C(O)NHR, C(O)NR₂, C(O)OH, C(O)OR, NHC(O)H, NHC(O)R, NRC(O)H, NRC(O)R, NHC(O)OH, NHC(O)OR, NRC(O)OH, NRC(O)OR, or a group selected from a $C_{1-6}$ aliphatic, a $C_{3-10}$ monocyclic or bicyclic cycloaliphatic, a $C_{6-10}$ monocyclic or bicyclic aryl, a 5-10 membered monocyclic or bicyclic heteroaryl, or a 5-10 membered monocyclic or bicyclic heterocyclyl, wherein said group is optionally substituted with 1-4 $J^X$, or two X, together with the carbon(s) to which they are attached, form a cyclopropyl ring or C=O; wherein X is not H when m is 0;

each $J^X$ is independently selected from halogen, OH, OR, NO₂, NH₂, NHR, NR₂, SH, SR, CN, C(O)NH₂, C(O)NHR, C(O)NR₂, C(O)OH, C(O)OR, NHC(O)H, NHC(O)R, NRC(O)H, NRC(O)R, NHC(O)OH, NHC(O)OR, NRC(O)OH, NRC(O)OR; and R⁹ is selected from H; halogen; OH; NO₂; NH₂; SH; CN; or a group selected from a $C_{1-6}$ aliphatic or a $C_{3-7}$ cycloaliphatic, wherein said group is optionally substituted with 1-6 occurrences of halogen, OH, NO₂, NH₂, SH or CN.

2. The compound or salt thereof according to claim 1, wherein Y is C(O) and the compound is of formula II:

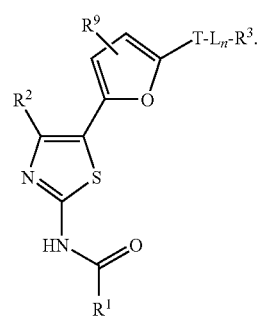

II

3. The compound or salt thereof according to claim 2, wherein R' is a $C_{1-3}$ aliphatic.

4. The compound or salt thereof according to claim 1, wherein R² is CH₃.

5. The compound or salt thereof according to claim 1, wherein said compound is of formula IIIa, IIIb or IIIc:

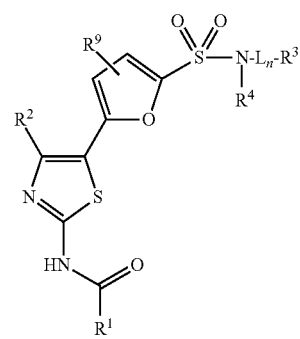

IIIa

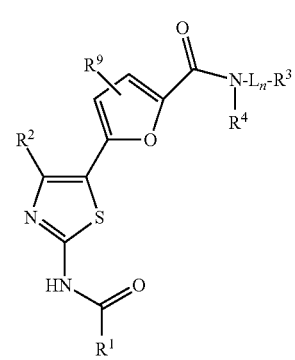

IIIb

-continued

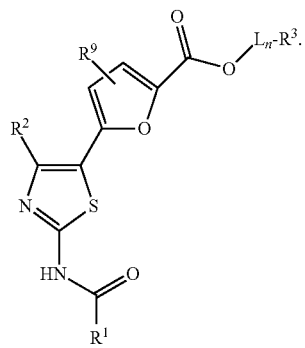
IIIc

6. The compound or salt thereof according to claim 1, wherein $R^3$ and $R^4$, together with the nitrogen to which $R^4$ is attached, form a monocyclic or bicyclic heterocyclyl or bicyclic heteroaryl selected from the following:

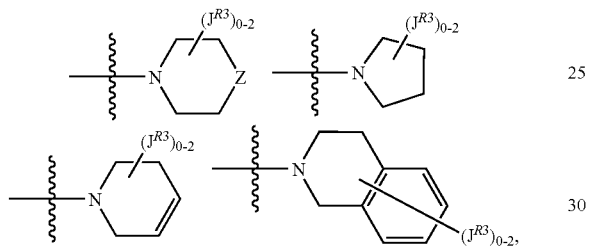

wherein Z is $CH_2$, NH, O or S, and wherein the hydrogens of said $CH_2$ of Z is optionally substituted by 1-2 occurrences of $J^{R3}$ and the hydrogen of said NH of Z is optionally substituted by $JR^3$.

7. The compound or salt thereof according to claim 1, wherein L is —$CH_2$—.
8. The compound or salt thereof according to claim 1, wherein n is 0.
9. The compound or salt thereof according to claim 1, wherein $R^3$ is a $C_{1-4}$ aliphatic, a $C_{3-6}$ monocyclic cycloaliphatic, phenyl, a 5-6 membered monocyclic heteroaryl, or a 5-10 membered monocyclic or bicyclic heterocyclyl, wherein $R^3$ is optionally substituted with 1-4 occurrences of $J^{R3}$.
10. The compound or salt thereof according to claim 9, wherein $R^3$ is a $C_{1-4}$ aliphatic, a $C_{3-6}$ monocyclic cycloaliphatic, phenyl, a 5-6 membered monocyclic heteroaryl, or a 5-6 membered monocyclic heterocyclyl, wherein $R^3$ is optionally substituted with 1-4 occurrences of $J^{R3}$.
11. The compound or salt thereof according to claim 10, wherein each occurrence of $J^{R3}$ is selected from halogen; OH; OR; CN; $NH_2$; NHR; $NR_2$; $C(O)NH_2$; C(O)NHR; $C(O)NR_2$; NHCOR; C(O)OR; C(O)OH; oxo; $(CH_2)_{0-3}$phenyl optionally substituted with halogen, OH, OR, $NO_2$, $NH_2$, SH or CN; or $C_{1-4}$ aliphatic optionally substituted with halogen, OH, OR, $NO_2$, $NH_2$, SH or CN.
12. The compound or salt thereof according to claim 1, wherein $R^8$ is selected from H, halogen, cyclopropyl, or a $C_{1-3}$ aliphatic optionally substituted with 1-3 occurrences of halogen or OH.
13. The compound or salt thereof according to claim 1, wherein $R^9$ is selected from H, OH, halogen, cyclopropyl, or a $C_{1-3}$ aliphatic optionally substituted with 1-3 occurrences of halogen or OH.

14. A compound selected from

1

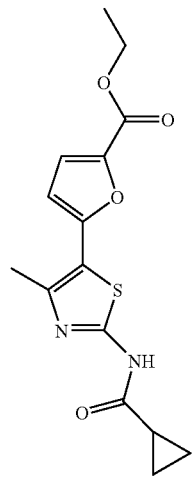

2

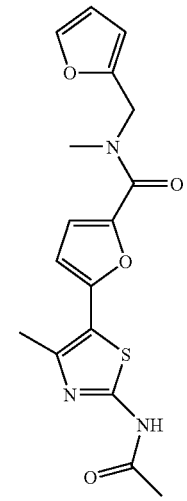

3

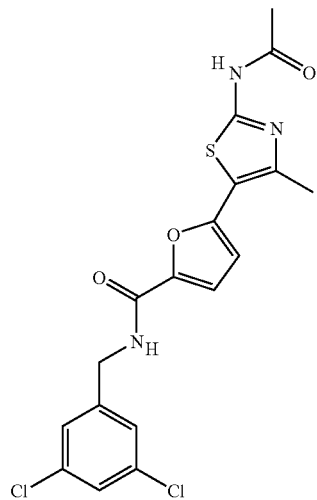

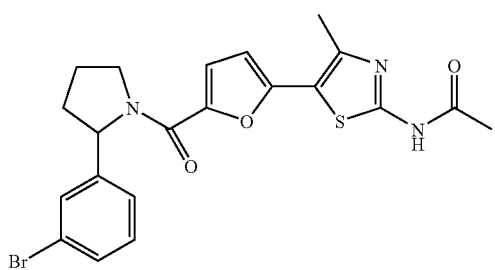
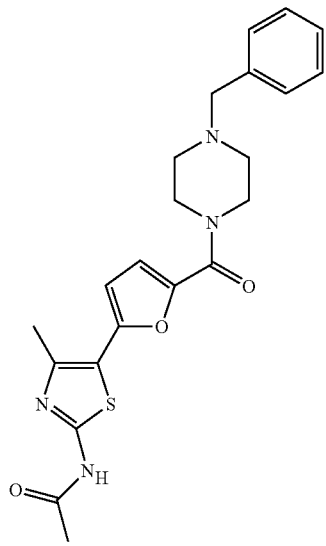
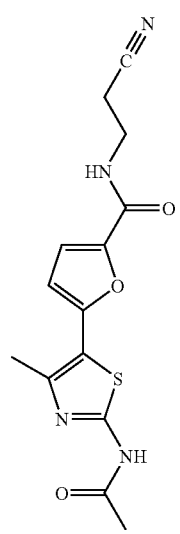
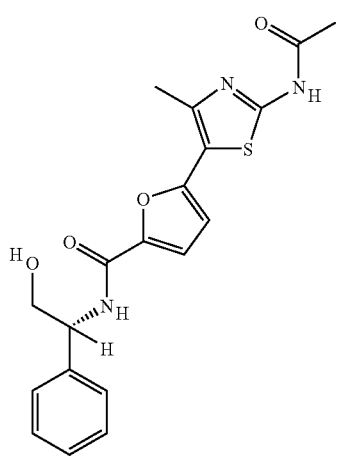

-continued
11
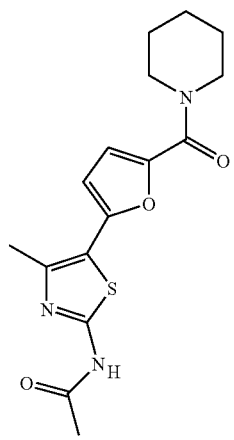
12
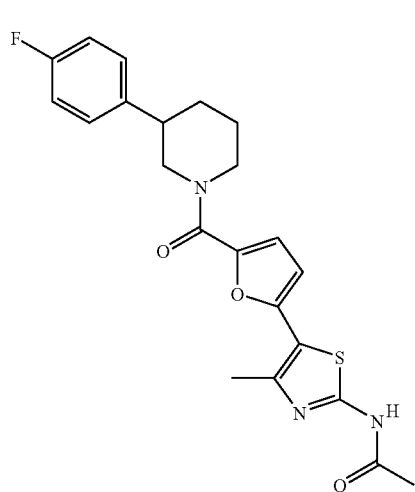
13
14
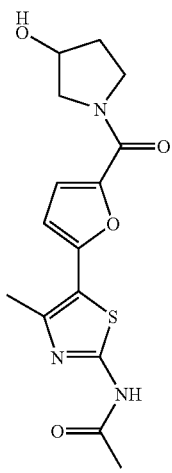
15
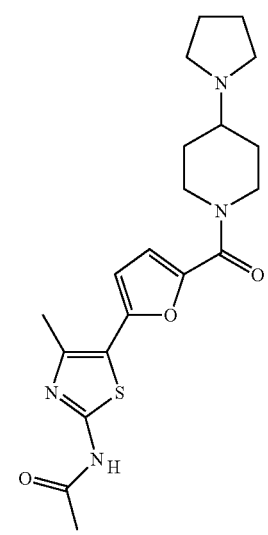
16
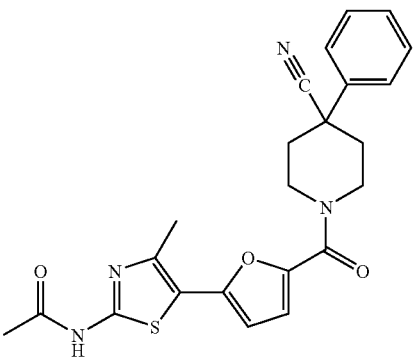

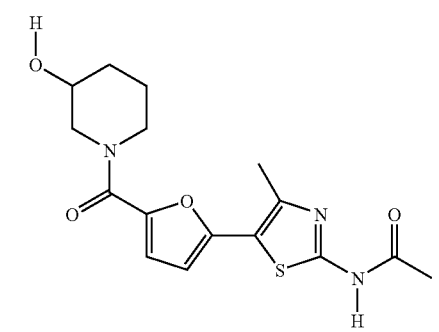
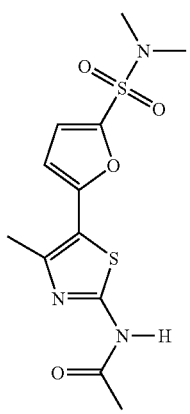
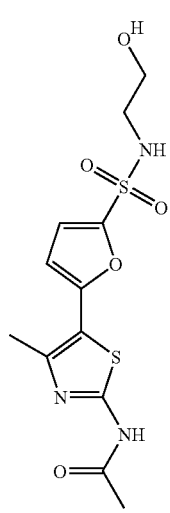
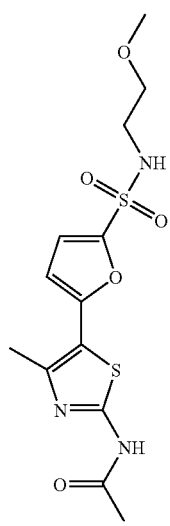

24
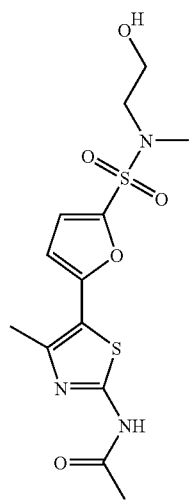
25
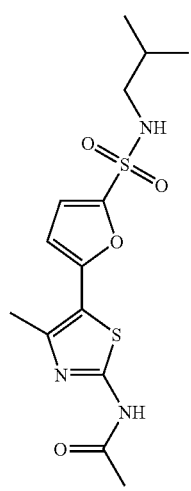
26
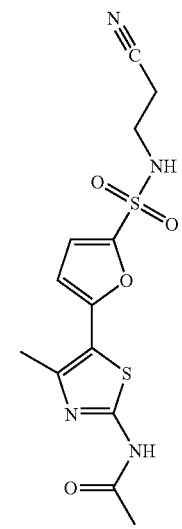
27
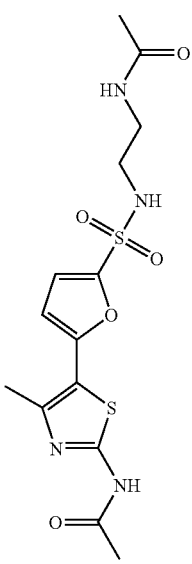
28
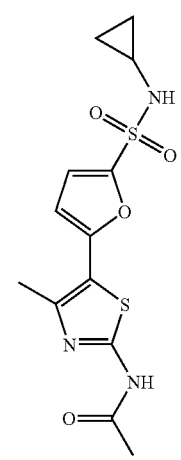
29
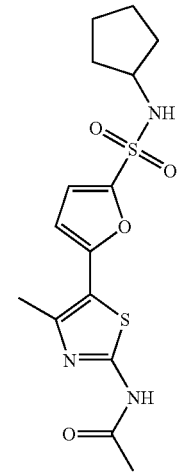

30
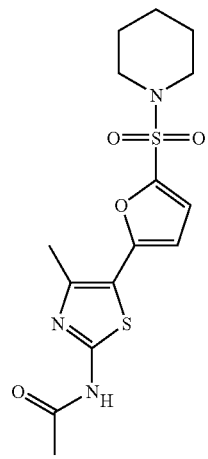
31
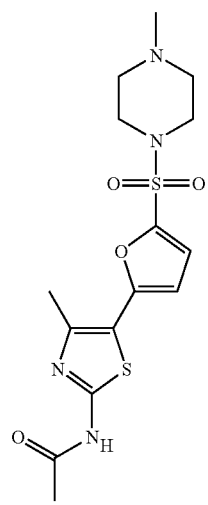
32
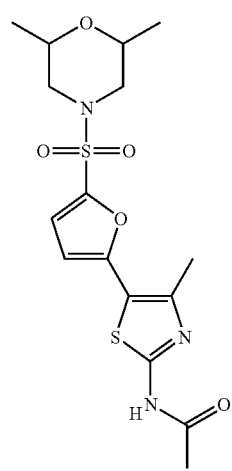
33
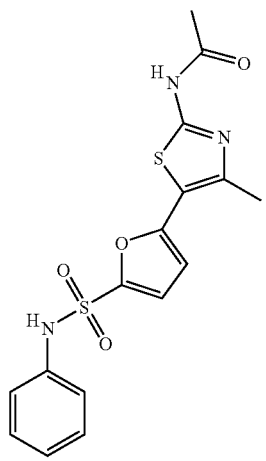
34
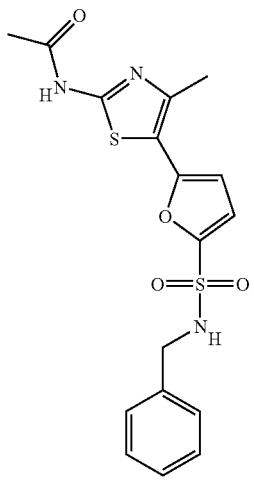
35
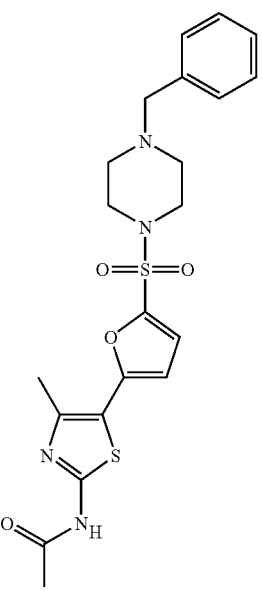

-continued
36
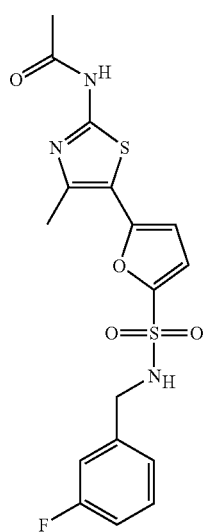
37
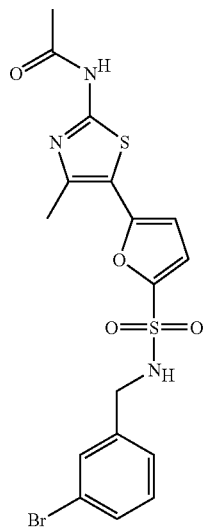
38
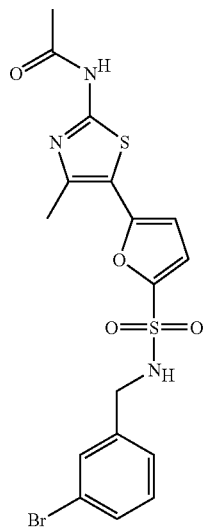
-continued
39
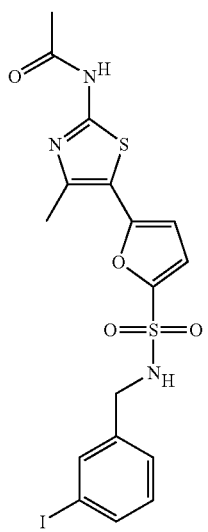
40
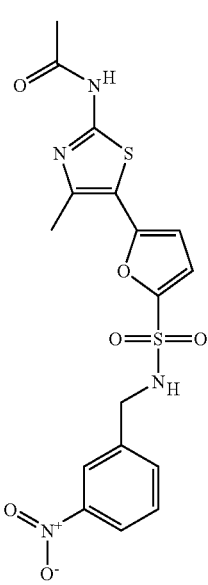
41
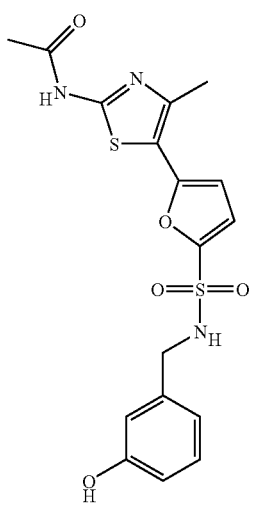

| 42 | 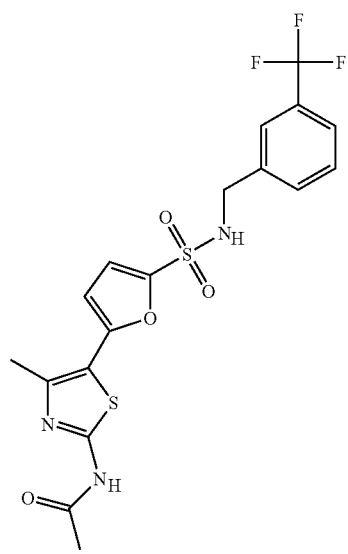 |
|---|---|
| 43 | 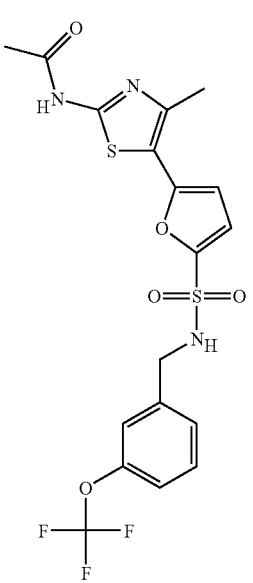 |
| 44 | 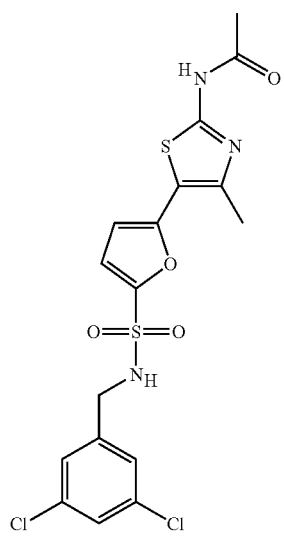 |
| 45 | 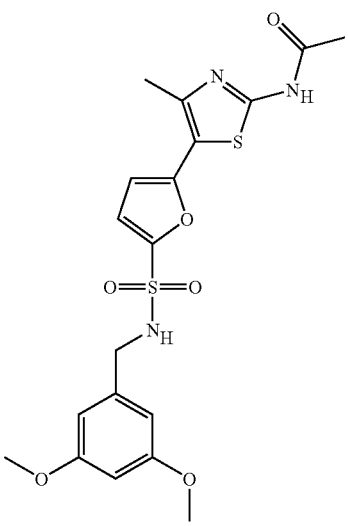 |
|---|---|
| 46 | |
| 47 | 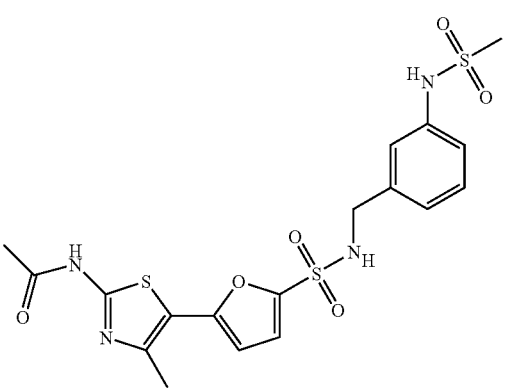 |

48
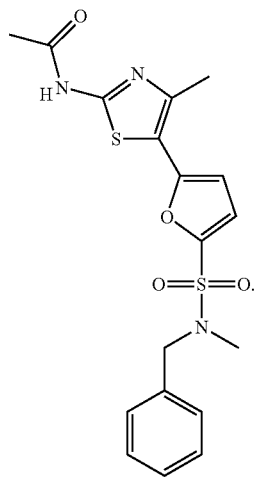
51
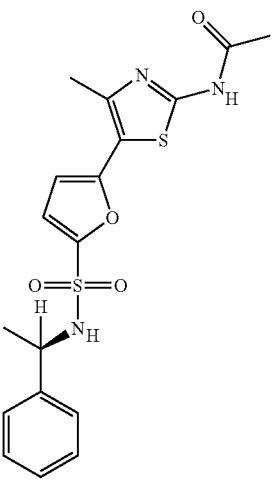
15. A compound selected from
49
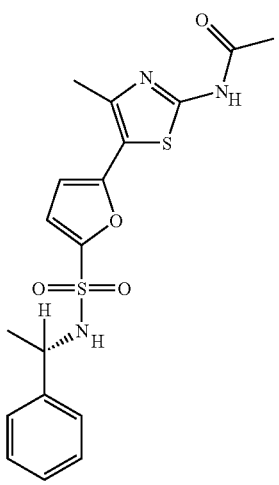
52
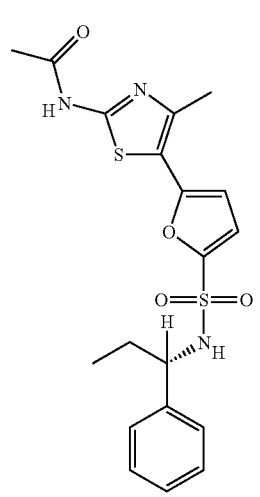
50
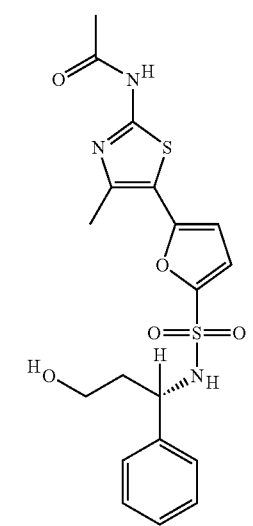
53
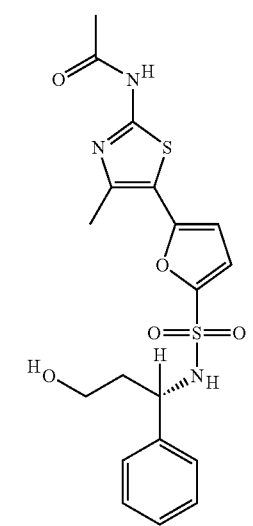

54
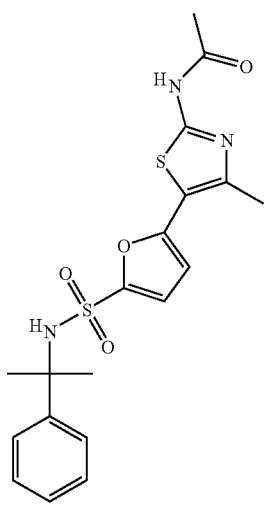
55
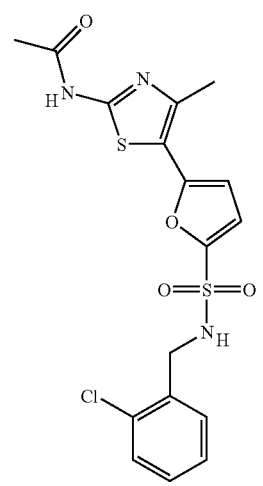
56
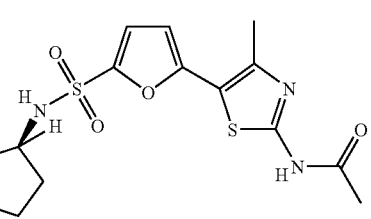
57
58
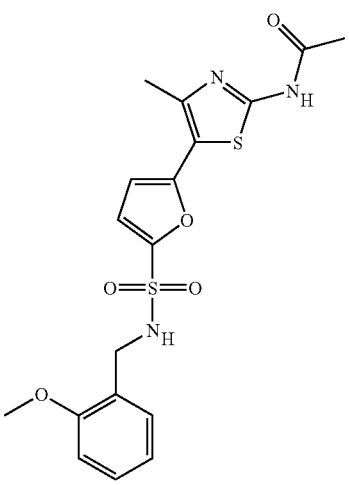
59
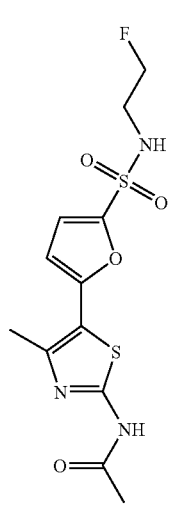
60
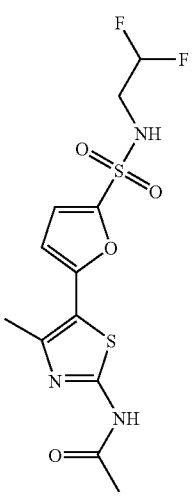

81
-continued
61
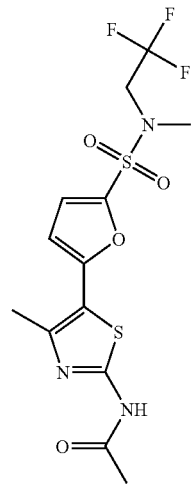
62
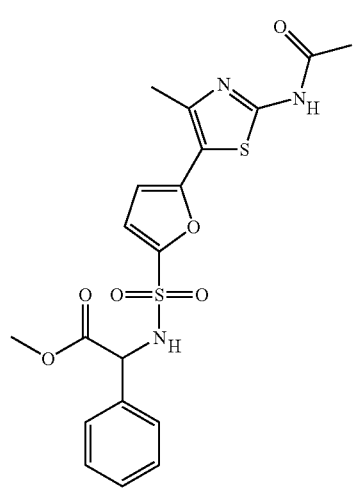
63
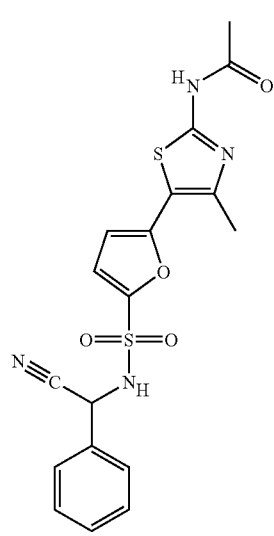
82
-continued
64
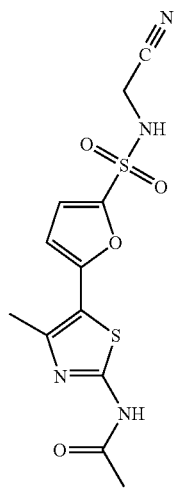
65
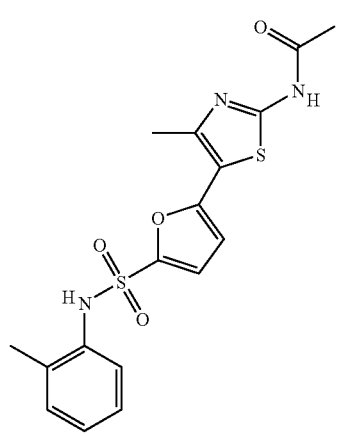
66
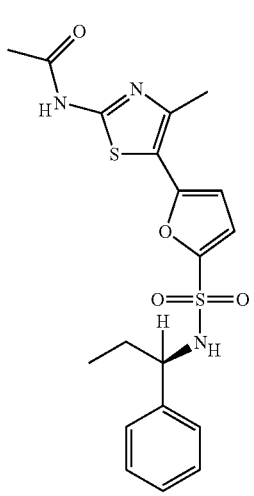

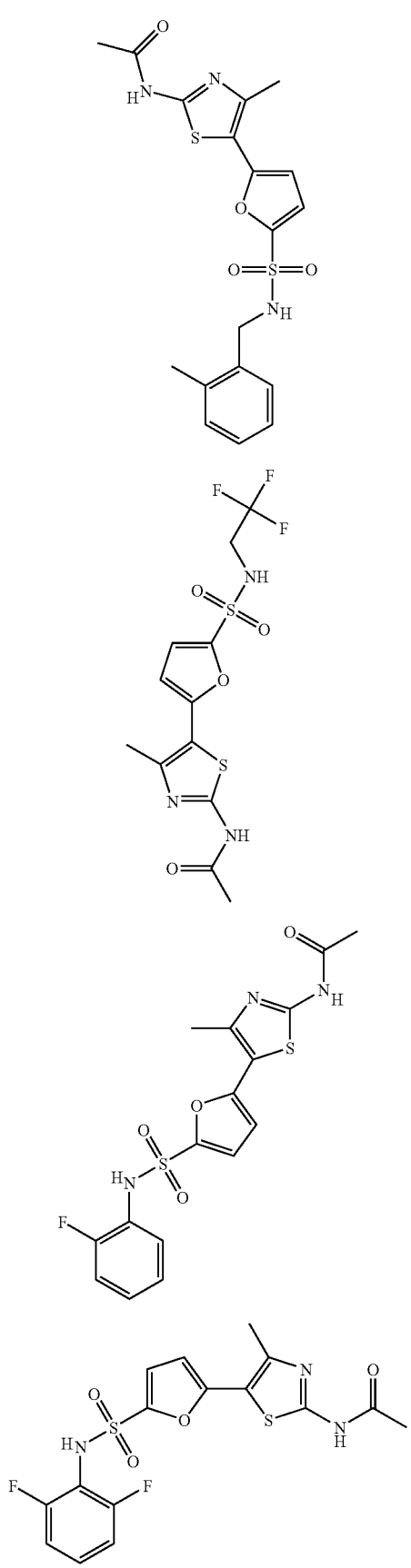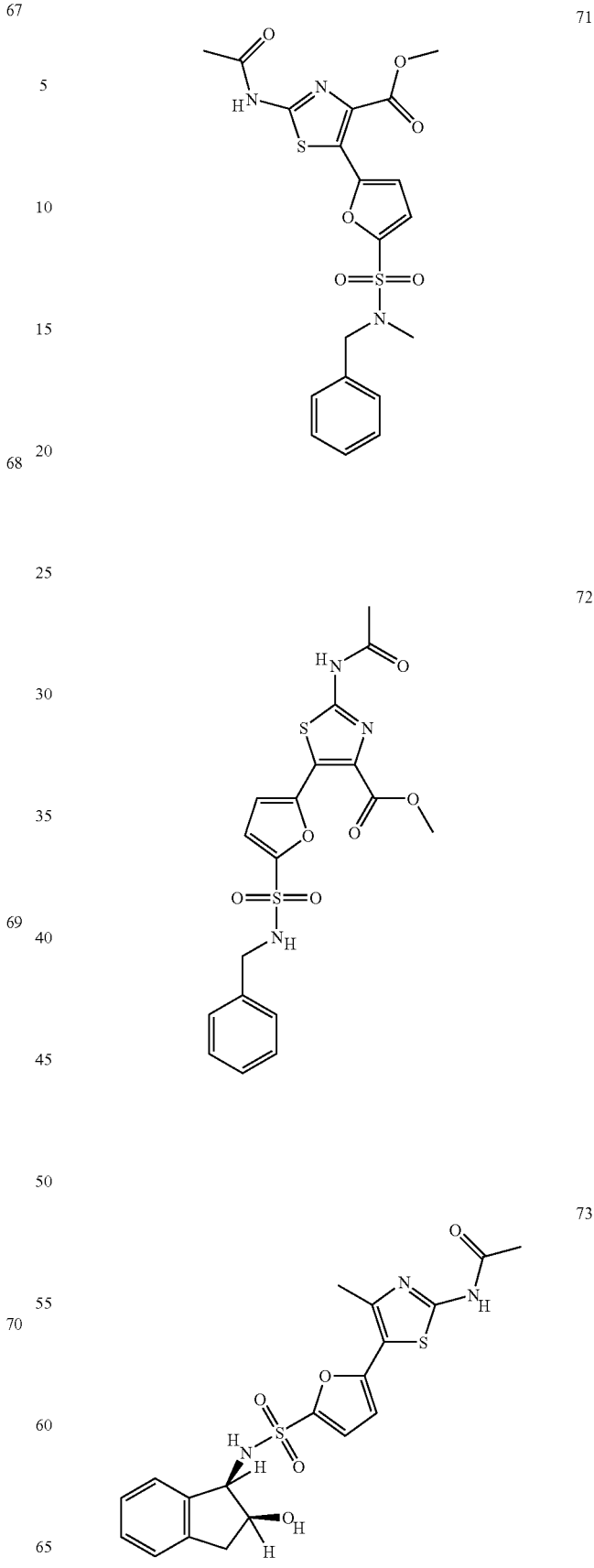

74

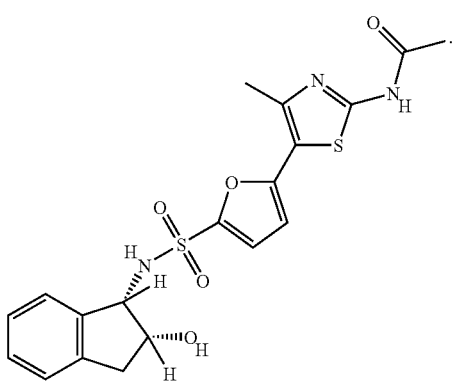

16. A pharmaceutical composition comprising a compound according to claim 1 and a pharmaceutically acceptable carrier, adjuvant, or vehicle.

17. A method of inhibiting phosphatidylinositol 3-kinase (PI3K) activity in a biological sample, comprising contacting said biological sample with a compound or salt thereof according to claim 1.

18. A method of treating or lessening the severity of a disease or condition selected from rheumatoid arthritis, systemic lupus erythematosus, atherosclerosis, lacrimal parotid gland syndrome, chronic obstructive pulmonary disease, pancreatitis, myocardial infarction, diabetes, multiple sclerosis or cancer comprising administering a compound according to claim 1 or a composition comprising said compound to a patient in need thereof.

* * * * *